(12) United States Patent
Nussinovitch et al.

(10) Patent No.: US 7,422,737 B1
(45) Date of Patent: Sep. 9, 2008

(54) POROUS FREEZE-DRIED HYDROCOLLOID BEADS CONTAINING VIABLE MICROORGANISMS FOR BIOLOGICAL CONTROL

(75) Inventors: Amos Nussinovitch, Rehovot (IL); Ilan Chet, Nes Ziona (IL); Cheinat Zohar Perz, Kiryat Ekron (IL)

(73) Assignee: Yissam Research Development Company of the Hebrew University of Jerusalem, Jerusalem (IL)

( * ) Notice: Subject to any disclaimer, the term of this patent is extended or adjusted under 35 U.S.C. 154(b) by 366 days.

(21) Appl. No.: 10/657,673

(22) Filed: Sep. 5, 2003

Related U.S. Application Data

(60) Provisional application No. 60/407,963, filed on Sep. 5, 2002.

(51) Int. Cl.
*A01N 63/00* (2006.01)
*C12N 11/02* (2006.01)
*C12N 11/10* (2006.01)
*C12N 11/08* (2006.01)
*C12N 11/04* (2006.01)

(52) U.S. Cl. .................... 424/93.4; 424/93.5; 435/177; 435/178; 435/180; 435/182

(58) Field of Classification Search .................... None
See application file for complete search history.

(56) References Cited

U.S. PATENT DOCUMENTS

| | | | |
|---|---|---|---|
| 2,441,729 A | 5/1948 | Steiner | 426/271 |
| 3,649,239 A | 3/1972 | Mitchell | 71/23 |
| 4,053,627 A | 10/1977 | Scher | 514/475 |
| 4,400,391 A | 8/1983 | Connick, Jr. | 514/521 |
| 4,401,456 A | 8/1983 | Connick, Jr. | 504/220 |
| 4,724,147 A | 2/1988 | Marois et al. | 424/93.5 |
| 4,764,371 A * | 8/1988 | Pusey et al. | 424/93.462 |
| 4,767,441 A | 8/1988 | Walker et al. | 504/117 |
| 4,818,530 A * | 4/1989 | Marois et al. | 424/93.5 |
| 4,879,239 A * | 11/1989 | Daggett et al. | 435/252.1 |
| 4,956,295 A | 9/1990 | Sudoma | 435/252.1 |
| 5,030,562 A * | 7/1991 | Elliott et al. | 435/29 |
| 5,919,695 A * | 7/1999 | Vedamuthu et al. | 435/252.5 |
| 6,068,867 A * | 5/2000 | Nussinovitch et al. | 426/102 |
| 6,204,049 B1 * | 3/2001 | Bennett et al. | 435/254.1 |
| 6,299,915 B1 * | 10/2001 | Nussinovitch et al. | 426/89 |
| 6,589,328 B1 * | 7/2003 | Nussinovitch | 106/205.1 |

OTHER PUBLICATIONS

C. Zohar-Perez et al. "Irregular textural features of dried alginate-filler beads" Food Hydrocolloids 18 pp. 249-258 (2004).
C. Zohar-Perez et al. "Mutual Relationships Between Soils and Biological Carrier Systems" Biotechnology and Bioengineering 92 (1) pp. 54-60 (2005).
V. Hershko et al. "The Behavior of Hydrocolloid Coatings on Vegatative Materials" Biotechnol. prog. 14 pp. 756-765 (1998).

* cited by examiner

*Primary Examiner*—David M Naff
(74) *Attorney, Agent, or Firm*—Winston & Strawn LLP

(57) ABSTRACT

The present invention provides cellular solid carriers comprising viable microorganisms capable of controlling plant pathogens. The cellular solid carriers are formed from water-soluble hydrocolloid beads dried under conditions which preserve their porosity, thereby allowing efficient release of microorganisms or diffusion of products derived from the microorganisms from the beads to the surrounding environment.

27 Claims, 13 Drawing Sheets

POROUS FREEZE-DRIED HYDROCOLLOID BEADS CONTAINING VIABLE MICROORGANISMS FOR BIOLOGICAL CONTROL

This application claims benefit of Provisional Application No. 60/407,963, filed Sep. 5, 2002.

FIELD OF THE INVENTION

The present invention provides cellular solid carriers comprising viable microorganisms capable of controlling plant pathogens. The cellular solid carriers are formed from hydrocolloid beads dried under conditions which preserve porosity, thereby allowing efficient release of microorganisms or diffusion of their products from the beads to the surrounding environment.

BACKGROUND OF THE INVENTION

The use of microorganisms such as fungi or bacteria for biological control in agriculture is known in the art. For example, microorganisms may be used for the improvement of crop growth and protection of plants in agriculture. Plant growth-promoting bacteria are disclosed for example in Bashan, 1998 (1). There are various factors limiting the effectiveness of biological control of microorganisms in agriculture, such as for example sensitivity of the microorganisms to UV radiation present in the field (2, 3). Moreover, direct use of antibiotics derived from biocontrol agents is limited due to UV sensitivity (4, 5).

The use of alginate gel technology to formulate agricultural products, pesticides, and food items is known in the art. For example, U.S. Pat. No. 4,053,627 describes the use of alginate gel discs for mosquito control, U.S. Pat. No. 3,649,239 discloses fertilizer compositions, and U.S. Pat. No. 2,441,729 teaches the use of alginate gels as insecticidal as well as candy jellies. In addition. U.S. Pat. Nos. 4,401,456 and 4,400,391 disclose processes for preparing alginate gel beads containing bioactive materials. None of these patents teaches the use of viable microorganisms as an active material incorporated in an alginate matrix.

U.S. Pat. Nos. 4,767,441, 4,818,530 and 4,724,147 disclose alginate gel pellets containing viable fungus capable of producing conidia when exposed to sufficient light and moisture. The resultant alginate gel pellets can then be dried and used to inoculate agriculture fields to kill selected plant pathogens. The alginate carrier disclosed in these patents comprises condensed pellets which lack a porous structure which is conducive to achieve optimal release of the active microorganisms or diffusion of active products produced by these microorganisms in field conditions. Furthermore, none of these patents disclose the incorporation of biological control bacteria in the alginate pellets.

One of the inventors of the present invention previously disclosed sponge-like, dry alginate beads obtained by freeze-drying alginate-based gel beads or other gels produced from water-soluble polymers (6 and U.S. Pat. No. 6,589,328). Freeze-drying of gel beads results in a low-density dried cellular product that is composed of many fused open and closed cells (compartments). The freeze-drying process creates the cell wall that contributes to the bead's mechanical properties and immobilization ability (7, 8). It was further disclosed by one of the present inventors that it is possible to preserve chitinolytic *Pantoae agglomerans* in a viable form by cellular dried alginate-based carriers (9).

There is an unmet need in the field of biological control for carriers of viable microorganisms effective in controlling plant pathogens which will permit efficient extended release of the viable microorganisms to the surrounding ground and which will protect the microorganisms against UV radiation.

SUMMARY OF THE INVENTION

The present invention relates generally to cellular solid carriers comprising viable microorganisms capable of controlling plant pathogens. More specifically it relates to dried cellular solid carriers comprising viable microorganisms capable of controlling plant pathogens.

According to a first aspect, the present invention provides dried hydrocolloids comprising viable microorganisms. According to preferred embodiments, the beads that are encompassed by the invention are porous. According to another aspect, the cellular solid carriers are configured for the release of the microorganisms themselves or products derived from the microorganisms.

According to yet another aspect, the present invention provides methods of controlling plant pathogens by exposing the pathogens to microorganisms or products derived from the microorganisms that are released into the environment from the cellular solid carriers of the present invention.

According to yet another aspect, the present invention provides a method of producing cellular solid carriers comprising dried hydrocolloid beads and viable microorganisms entrapped therein comprising: mixing a hydrocolloid solution with viable microorganisms; and drying said mixture under conditions which presence the porosity of said hydrocolloid beads, thereby forming dried cellular solid hydrocolloid beads comprising viable microorganisms entrapped therein.

According to yet another aspect, the present invention provides methods of increasing the viability of biological control microorganisms in field conditions comprising entrapping the biological control microorganisms within solid cellular carriers comprising dried hydrocolloid beads prior to the application of said microorganisms to the agricultural field, thereby increasing the viability of biological control microorganisms in field conditions.

According to one embodiment, the cellular solid carriers comprise hydrocolloid beads dried under conditions which preserve porosity, thereby allowing efficient release of microorganisms or diffusion of their products from the beads to the surrounding environment after exposure to moisture. According to another embodiment, the cellular solid carriers comprise hydrocolloid beads dried under conditions which preserve their porosity, thereby allowing extended release of microorganisms or diffusion of their products from the beads to the surrounding environment after exposure to moisture.

According to currently preferred embodiments, freeze-drying is the preferred method for drying the hydrocolloid beads in order to preserve their porosity. It is now disclosed that freeze-drying of gel beads results in a low-density dried cellular product that is composed of many fused open and closed cells. This cellular structure enables the controlled release or extended release of microorganisms or their products from the matrix upon exposure to moisture and preserves the viability of the microorganisms.

It is to be understood that while the solid carriers of the present invention are referred to throughout the specification and claims as "beads", this term is intended to be construed in a non-limitative fashion, and does not imply any requisite geometry, specific shape or size of the product. It is noted that the size of the beads may vary from several microns to several hundred of microns. Preferably, the size of the beads is between 50 microns to 500 microns.

According to various embodiments, the cellular solid carriers of the present invention are prepared from hydrocolloid gels. A preferred hydrocolloid gel for use in the present invention is alginate. However, other hydrocolloid gels, preferably water-soluble hydrocolloid gels may be used. Suitable water-soluble hydrocolloid gels are for example agarose, low methoxy pectin (LMP), polyvinyl alcohol (PVA), Carrageenan, and xanthan plus locust bean gum (LBG).

According to preferred embodiments of the present invention the beads further comprise a cryopreservative, which is mixed with the hydrocolloid gel solution prior to drying. According to currently more preferred embodiments of the present invention the beads further comprise glycerol, which is mixed with the hydrocolloid gel solution prior to drying. It has been found that glycerol acts as a cryopreservative to enhance the viability of the microorganisms, while simultaneously acting to maintain the porosity of the gels. Preferred concentrations glycerol in the gel solution prior to drying range from 10-50% (w/w), preferably from 20-40% and most preferably about 30%.

The dried hydrocolloid beads comprising viable microorganisms capable of controlling plant pathogens of the present invention exhibit significant advantages over the existing art. The dried cellular solid carriers comprising the viable microorganisms have an extended shelf life. The extended shelf life is obtained in part due to the low percentage of moisture present in the dried hydrocolloid beads comprising viable microorganisms prior to the application thereof to a plant or a field. The residual moisture in the dried hydrocolloid beads comprising the microorganisms is between zero to twenty percent, preferably between zero to twelve percent.

In the beads of the invention, having this low residual moisture, the viability of the microorganisms is very high. In preferred embodiments wherein the dried cellular solid carriers comprise glycerol not less than 50% of the microorganisms remain viable for at least one year of storage at temperatures below −18° C. Preferably, not less than 75% of the microorganisms remain viable for at least one year of such storage and most preferably, around 90% to 95% or more of the microorganisms remain viable for at least one year of such storage. Furthermore, preferred embodiments include retention of these proportions of microorganism viabilities for at least 2 to three years of storage as dried beads at temperatures at or below ~18° C. If desired, lower storage temperatures to as low as −70° C. can be used to maintain microorganism viabilities for longer storage times.

Another important advantage of the present dried hydrocolloid beads containing the viable microorganisms over the existing art is the sustained release characteristics upon exposure of the beads to moisture. According to a preferred embodiment of the present invention, the preparation of the dried hydrocolloid beads comprises a step of freezing the beads followed by freeze-drying. Freeze-drying of gel beads results in a low-density dried cellular product that is composed of many fused open and closed cells. This cellular structure enables the controlled release of microbial cells or their products from the matrix upon exposure of the beads to moisture. Thus, the preparation process of the dried hydrocolloid beads preserves the porosity of the gel, thereby allowing efficient release of microorganisms or diffusion of their products from the beads into the surrounding ground upon exposure of the beads to moisture. Other methods for drying the beads while preserving the porosity of the beads are within the scope of the present invention. Such methods include for example vacuum drying, fluidized bed drying or air drying.

The porosity of the hydrocolloid beads also permits the diffusion of any products secreted by the microorganisms to the ground. Such products are for example enzymes or antibiotics produced by the immobilized microorganisms which are effective in the control of plant pathogens. One exemplary active enzyme is for example chitinase which may be effective in the control of plant pathogenic fungi carrying chitin as the major structural component of their cell walls. Other examples of enzymes which may be effective in the control of plant pathogens are gluconases and proteases. Antibiotics and other agents effective in the control of plant pathogens which may be produced by the immobilized microorganisms are for example pyrolnitrin, pyrolniteorin, phenazines, DAPG (2,4, diacetylfluoroglucinol), ferrichrome A or desferrioxamine B.

According to another aspect of the present invention, the dried cellular solid hydrocolloid beads further comprise suitable nutrients or fillers incorporated within the dried cellular solid hydrocolloid beads. The nutrient is selected so as to support the growth of the particular microorganism or microorganisms of choice within the hydrocolloid beads.

According to one embodiment, the incorporation of chitin as a nutrient for chitinolytic immobilized bacteria facilitates the sustained bacterial production of chitinase within the beads, thereby allowing continuous release of the active bacteria or of the active product into the ground. Other nutrients or fillers suitable in the present invention are for example pectin, cellulose, lignin, starch, bentonite, kaolin, glycerol or low fat milk.

According to another aspect of the present invention, the cellular solid hydrocolloid beads preserve the viability of the immobilized microorganisms in field conditions. Specifically, the cellular solid hydrocolloid beads are effective in protecting the immobilized microorganisms from UV radiation. Thus, the immobilized microorganisms may be effective as biological control of plant pathogens even after long exposure to UV radiation in field conditions.

The dried cellular solid hydrocolloid beads of the present invention are suitable for incorporating a wide range of biological control microorganisms. Specifically, both bacteria and fungi may be incorporated within the beads.

According to certain preferred embodiments, the hydrocolloid beads comprise bacteria such as *Pantoae agglomerans, Serratia marcescens, Bacillis Spp., Enterobacter Spp., Azotobacter, Azospirillum* and *Pseudonionias*.

According to other embodiments, the hydrocolloid beads comprise fungi effective against plant pathogens. According to certain preferred embodiments the hydrocolloid beads comprise fungi such as *Trichoderma harzianum, Trichoderma lignorum* and *Trichoderma viride*.

As disclosed herein, the present dried hydrocolloid beads comprising viable microorganisms capable of controlling plant pathogens exhibit a superior effectiveness against plant pathogens, including pathogenic fungi. Plant pathogens that may be treated according to the principles of the present invention include for example *Pythium aphanidermatum, S. scabies, Verticillium dahliae, Verticillium albo-atrum, Fusarium solani, Rhizoctonia solani, Cylindrocladium floridanum, Clavibacter michiganense subsp. sepidonicum Phytophthora megasperma pv. glycinea,* race 1, *Pythium spp., Septoria spp.* or *Sclerotinia*.

A preferred method according to the invention comprises applying a combination of two or more strains of biological control microorganisms to the susceptible crop. The combination of at least two strains of biological control microorganisms reduces the development of resistant forms of the pathogen on the crop. The suppressive biological control microorganisms of the combination are compatible with each other in that one strain does not inhibit the growth of the other strain. It is preferred that at least two of the strains of the combination are capable of co-growth when combined together on the susceptible crop. It is further preferred that at least two of the strains of the combination do not produce inhibitory compounds against each other.

According to certain embodiments, the combination of two or more microorganisms can be applied wherein they are incorporated into the same beads. According to alternative embodiments the combination of two or more microorganism can be incorporated into separate beads applied to the same crop.

It will be appreciated by the skilled artisan that the dried cellular hydrocolloids comprising viable microorganisms will become activated upon exposure to moisture in the environment.

These and further embodiments will be apparent from the detailed description and examples that follow.

DETAILED DESCRIPTION OF THE PREFERRED EMBODIMENTS

Figure 1:
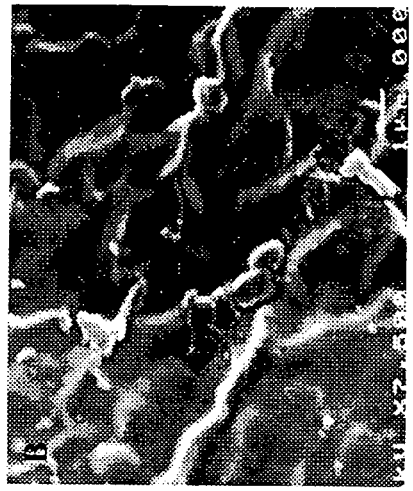
FIG. 1 shows the presence of *Pantoae agglomerans* cells within (A) and on the inner surfaces (B) of freeze-dried alginate beads (arrows indicate bacteria position).
Figure 1:
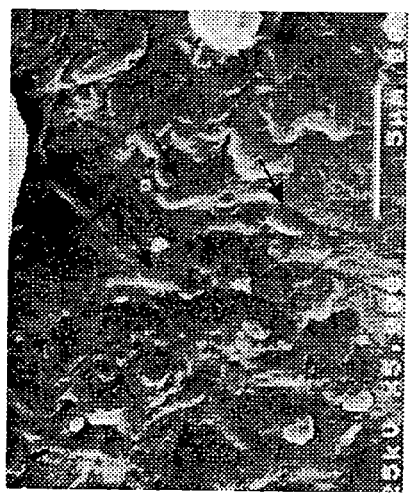

The present invention provides cellular solid carriers comprising viable microorganisms capable of controlling plant pathogens. The cellular solid carriers are formed from hydrocolloid beads dried under conditions which preserve their porosity, thereby allowing efficient release of microorganisms or diffusion of their products from the beads to the surrounding environment. Furthermore, the porosity of the beads preserves the viability of the entrapped microorganisms in field conditions.

It is noted that the term "hydrocolloids" referred to in the present invention includes gums, water soluble polymers, polysaccharide gels and mucilages.

According to currently preferred embodiments freeze-drying is the preferred method for drying the hydrocolloid beads in order to preserve the porosity of the beads. The degree of porosity enables the controlled release of microorganisms or their products from the matrix. It is also preferred to store the dried hydrocolloid beads below 0° C., preferably at temperatures below −20° C. prior to the application into the ground in order to preserve the viability of the entrapped microorganisms over time. To obtain the longest maintenance of viability time, storage at lower temperatures, such as to as low as −50° C., −70° C. or lower, can be used for this purpose.

The present invention is based in part on the surprising finding by the inventors that the bacterial and fungal biocontrol agents immobilized in freeze-dried alginate gel beads are protected from UV radiation. *T. harzianum* and *P. agglomerans* were chosen as model microorganisms to explore the protection capacity for fungal (spores) and bacterial (Gram-negative non-spore formers) biocontrol agents against UVC light. UVC was chosen for this study since it is lethal to most microorganisms in the range of 250 to 260 nm, including bacteria, viruses, protozoa, mycelial fungi, yeast and algae.

In one aspect, the present invention is related to a method for controlling plant pathogens in an agricultural setting, comprising: applying dried cellular hydrocolloid carriers comprising viable microorganisms to a crop, wherein said microorganisms or an active product produced by said microorganisms are effective for controlling plant pathogens.

The methods of the invention comprise providing natural means of biologically controlling a plant disease in a susceptible crop. According to these methods, an effective growth-inhibiting amount of suppressive biological control microorganisms entrapped within a cellular solid carrier of the invention are applied to the susceptible crop to inhibit the growth of one or more species and/or strains of a pathogenic plant microorganism. The application of the suppressive biological control microorganisms can also provide for growth enhancement either directly or indirectly. Growth enhancement can be observed by a significant increase in yield and/or quality of the plant product. While not meant to limit the invention in any way, it is believed that growth enhancement can occur indirectly by inhibiting the growth of deleterious pathogens in the soil.

A suppressive strain of biological control microorganism is applied to the crop in an amount effective to inhibit the growth of a pathogenic strain of a plant pathogenic organism. The suppressive strain is preferably capable of substantially outgrowing and/or inhibiting the growth of the pathogenic strain.

The dried hydrocolloid beads of the invention include at least one suppressive strain of biological control microorganism in an amount effective to inhibit the growth of a plant pathogenic microorganism on a vegetable or other crop, in combination with a physiologically-acceptable carrier. The suppressive strain of the biological control microorganism is preferably capable of outgrowing and/or inhibiting the growth of a plant pathogenic microorganism.

In a preferred method according to the invention, a combination of two or more strains of biological control microorganisms are applied to the susceptible crop. The combination of at least two strains of biological control microorganisms reduces the development of resistant forms of the pathogen on the crop. The suppressive biological control microorganisms of the combination are compatible with each other in that one strain does not inhibit the growth of another strain. It is preferred that at least two of the strains of the combination are capable of co-growth when combined together on the susceptible crop. It is further preferred that at least two of the strains of the combination do not produce inhibitory compounds against each other.

Plant pathogens susceptible to treatment by the methods of the present invention include for example *S. scabies, Verticillium dahliae, Verticillium albo-atrum, Fusarium solani, Rhizoctonia solani, Cylindrocladium floridanum Clavibacter michiganense subsp. sepidonicum, Phytophthora megasperma* pv. *glycinea* race 1, *Pythium* spp., *Septoria* spp., *Sclerotinia* and other like pathogens and diseases associated with these pathogens. These plant pathogens are associated with diseases such as wilts, root rot, seedling blights, and damping off For example *V. dahliae* causes wilt and *Rhizoctonia solani* causes root rot and seedling blight. The plants affected by these pathogens preferably include vegetables, soybeans, wheat, alfalfa, sugar beets, hybrid poplars and corn.

Examples of crops susceptible to seedling blight diseases include alfalfa, field beans, soy beans, corn, sugar beets; pine, spruce and conifer nurseries; bedding plants and greenhouses; vegetables such as potatoes and tomatoes; turf and turf grasses; wheat and other small grains such as oats, barley and the like. When the beads comprising the biological control microorganisms are applied to inhibit seedling blight diseases, it is preferably applied as a seed treatment or to plants or to soil in liquid or granular form.

The beads comprising the biological control microorganisms may be applied, for example, to vegetable or other plant seeds, to the soil in close proximity to the plants or seeds, by spraying or by trickle-drip irrigation. Seeds can be treated by mixing with the suppressive biological control microorganisms entrapped within the hydrocolloid beads. The biological control microorganisms may be applied to the soil using any method which brings the biological control microorganisms in contact with the plant or in proximity to its environment. For example, a furrow may be opened in the soil and the beads containing the biological control microorganisms may be placed into the furrow such that the biological control microorganism come into contact with the seed portion of the vegetable. In a preferred method, the beads containing at least one strain of biological control microorganisms is applied to the soil or seeds and/or directly onto the crop. In another embodiment, the dried beads comprising at least one strain of biological control microorganisms are suspended in a fluid suitable for application by spraying onto a field or a crop.

For control of scab disease, the beads comprising the biological control microorganisms are preferably applied to the soil or as a seed treatment, or both at planting, and is preferably applied in successive growing seasons. The application of the beads can also be combined with traditional crop management techniques including crop rotation. For example, the beads comprising the biological control microorganisms can be applied to a crop such as potatoes, to the soil, or to the seeds in the first year. In subsequent growing seasons such as 1 to 3 years, a different crop can be grown in the same plot of land with or without additional applications of the beads. When the susceptible crop is replanted in the same plot of land, after one or more growing seasons, the crop, seed, or soil can be optionally reinoculated with the beads comprising the biological control microorganisms to achieve a significant inhibition of scab disease.

The beads comprising the biological control microorganisms can preferably persist in the soil, in the seed population, or in the rhizosphere for a period of time sufficient to inhibit disease development with or without multiple applications. The period of time will depend, in part, on the disease and microorganism causing the disease. For inhibition of scab disease, preferably beads comprising the biological control microorganisms can persist after one application for about 2 weeks to about 4 years, more preferably about 12 weeks to about 3 years are selected.

The beads comprising the biological control microorganisms preferably include about $10^3$-$10^{10}$ colony forming units (CFU) of bacteria or spores per bead. For immediate action, it is preferable to use beads comprising at least $10^9$ CFU/bead while for delayed action it is preferable to use beads comprising about $10^3$ to about $10^4$ CFU/bead.

According to various embodiments, the cellular solid carriers of the present invention are made from hydrocolloid gels. A preferred hydrocolloid gel for use in the present invention is alginate or any water soluble salt of alginic acid. However, other water-soluble hydrocolloids may be used. Sodium alginate is the most preferred alginate but other water soluble salts of alginic acid such as potassium alginate may be used. Alginate concentration in the gel mixture prior to drying may be from 0.5 to 3% (w/w), preferably 2% (w/w).

Metal cations that react with and cause gelation of sodium alginate solutions are for example the cations of calcium, barium, zinc, copper, aluminum, and mixtures of these. A water soluble calcium salt such as calcium chloride is preferred for the process of this invention because this compound is not toxic to the biological control microorganisms. An effective concentration range of calcium chloride gellant bath, also called the salt solution, is 1% to 15% (w/v) but, 1% to 5% is preferred. It is noted that the higher the concentration of the salt the faster the reaction with the alginate.

Various organic and inorganic fillers can be used in preparing the carriers of the present invention. Other adjuvants that may be of use when incorporated are selective fungistats, antibiotics, nutrients, materials that prevent damage to the viable microorganisms during freezing, materials that stimulate spore production, viscosity modifiers, materials that control the hardness of the beads or their cell wall thickness, or materials that control the rate of biodegradation or disintegration. Chitin is particularly useful as a nutrient but other nutrients or fillers such as pectin, cellulose, starch, glycerol, low fat milk or lignin are within the scope of the present invention.

Preferred embodiments according to the invention comprise glycerol which simultaneously preserves the porosity of the freeze dried bead while acting as a cryopreservative. It is preferable to add glycerol to the hydrocolloid gel comprising the biological control microorganisms. The advantages of adding glycerol are to prevent damage to bacteria during freezing, to control the porosity of the beads and to control cell wall thickness of the dried cellular solid.

According to a preferred embodiment, the preparation of the dried hydrocolloid beads containing the biological control microorganisms comprises a step of freezing the beads followed by freeze-drying. Freeze-drying of the gel beads results in a low-density dried cellular product that is composed of many fused open and closed cells. The dried beads may be stored for extended periods of time. Methods for freezing the beads are for example freezing below or at −18° C., blast freezing, fluidized bed freezing and liquid nitrogen freezing and then dried by techniques such as by lyophilization, drying in a vacuum, or drying by fluidized bed method. Other methods of drying without freezing such as vacuum drying, fluidized bed drying or air drying are also within the scope of the present invention.

When made in this manner, the dried hydrocolloid beads have a desired internal microporosity in which the microorganisms reside. After application of carrier or beads to the plants or soil, the surrounding conditions cause the microorganisms to multiply and to secrete products into the hydrocolloid. Gradually, these products are released into the soil where they can act on the plant pathogens. In addition, exposure of the dried hydrocolloids to moisture can assist in the swelling or degradation of the hydrocolloid to assist in releasing the microorganism or their products into the soil or onto the plants. In this manner, a delayed and sustained release of the microorganisms is achieved, thereby efficiently treating plant pathogens over time.

EXAMPLES

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Immobilization of *Trichoderma harzianum* T-203 and *Pantoae agglomerans* IC1270 in dried alginate beads afforded significant protection against UVC toxicity Materials and Methods:

Culture medium and growth of microorganisms: For entrapment, the previously isolated bacterium *Pantoae agglomerans* strain IC1270 (10) and the fungus *Trichoderma harzianum* T-203 (11) were used as model microorganisms. The bacteria were grown in liquid (for the preparation of cell stocks) or on solid (2% w/v agar) nutrient broth (NB) and agar (NA), respectively. Cells were grown in NB for 24 h with aeration at 28° C. to a final concentration of $5 \times 10^8$ to $1 \times 10^9$ cells/ml. The fungus was grown on solid potato dextrose agar (PDA) for 7 days at 28° C. Spores were harvested by washing the medium surface with deionized sterile water, gently detaching them with a soft sterile brush and then filtering the suspension through multi-layered gauze in order to basically eliminate the mycelia in the suspension. Spores and bacterial cells were then separated by centrifugation at 4100×g (5000 RPM) in a refrigerated superspeed centrifuge (Universal 16R, Hettich, Gartenstrabe, Tuttlingen) for 15 min at 20° C. and suspended in sterile distilled water.

Preparation of the immobilization complex: Alginate with a molecular mass of 60 to 70 kDa, containing 61% mannuronic acid and 39% guluronic acid (Sigma, LV, St. Louis, Mo.), was dissolved in distilled water (2% w/w). Glycerol (30% w/w, final concentration) was added to the alginate solution (2% w/w, final concentration). For the alginate-filler bead preparation, a colloidal chitin suspension prepared by the method of Rodriguez-Kabana et al. (12), bentonite (Sigma, average particle size 10 μm) or kaolin (Sigma, average particle size 0.5 μm) were added to the alginate and alginate-glycerol solutions to a final concentration of 0.5% (w/w). All mixtures were sterilized by autoclaving.

Strain IC1270 (~$10^{11}$ cells/ml) or T-203 (~$10^9$ spores/ml) were then added at a 1:9 volumetric ratio to the different sterile alginate solutions. Those final mixtures were dripped into a 1% (w/w) sterile solution of calcium chloride and stirred for 30 min (the volumetric ratio between the alginate mixture and the calcium chloride solution was 1:50). A spontaneous cross-linking reaction produced spherical beads with a diameter of 2.9 to 3.6 mm, containing either ~$10^7$ CFU/bead (fungi) or ~$10^9$ cells/bead (bacteria). The beads were removed from the calcium chloride solution and washed twice with sterile distilled water through a strainer (funnel) to remove excess ions from their surface. Then, the beads were frozen at −80° C. for 1 h before freeze-drying, which was carried out at −50° C. at a pressure of 1.1 Pa (Martin Christ model ALFA I-5; Osterode am Harz, Germany).

UV irradiation: Fungal spores immobilized in alginate-glycerol and alginate-glycerol-chitin dried beads and bacterial cells immobilized in alginate-glycerol, alginate-glycerol-chitin, alginate-glycerol-bentonite and alginate-glycerol-kaolin dried beads were exposed to UVC (254 nm) radiation under sterile conditions at room temperature (20 to 25° C.) and relative humidity (50 to 55%). As a control, droplets with a volume of 100 μl containing fungi or bacteria suspended in water or alginate solution were irradiated. The beads or the droplets were placed on a sterile plastic Petri dish (9 cm diameter) and the experiment was performed in a laminar air-flow hood in order to maintain sterility during the irradiation. UVC was delivered for up to 420 min, at a UV flux rate of 21 J/(m²·min) by Mineralight lamp, model UVS 11 (Ultra violet Products, Inc., San Gabriel, Calif.). UV fluency was determined with a UVC radiometer model 1L-1400 (International Light Inc., Newburyport, Mass.).

Bacterial enumeration in the freeze-dried beads: Viable bacterial and spore counts were taken before and after UV exposure. For each UVC exposure three beads or droplets were removed and enumerated. To dissolve the beads for bacterial and fungal counts, they were immersed in a 2% (w/w) sterile sodium citrate solution and vigorously shaken (400 rpm) to total dissolution (~20 min). The released bacteria and spores were immediately serially diluted, plated on NA or on PDA amended with 1 μl/ml Igepal (Sigma), respectively, and incubated for 24 h at 28° C. for colony formation and enumeration.

UVC transmission analysis: To evaluate the beads' transparency to UVC light (254 nm), freeze-dried alginate, alginate-chitin, alginate-bentonite, alginate-kaolin, alginate-glycerol, alginate-glycerol-chitin, alginate-glycerol-bentonite and alginate-glycerol-kaolin flat matrices (2.9±0.3 mm diameter) were prepared. The alginate solutions were transferred to a tubular cellulose membrane (MFPI, San Antonio, Tex., nominal MWCO: 12,000-14,000, width: 76 mm, wall thickness: 40 μm, diameter: 48.4 mm) and immersed in a 1% (w/w) solution of calcium chloride for 24 h to create alginate gel-based sleeves. The flat matrices were created by slicing the gel sleeves with two parallel razor blades. These matrices were freeze-dried as aforementioned resulting in about 3-mm dried flat matrices. We chose 3-mm films to simulate the maximal thickness of the bead. The transmission of those matrices was determined using the UVC radiometer.

Temperature Measurements During UVC Irradiation

The temperature at the center and on the surface of the beads during UVC irradiation was determined by data-logging K/J thermometer and appropriate thermocouples (TES Electrical Electronic Corp., Taipei, Taiwan).

Electron micrographs and image analysis: To study the beads' structure and wall thickness, scanning electron microscopy (SEM) was performed in a Jeol JSM 35C SEM (Tokyo, Japan) at an accelerating voltage of 15 kV and a working distance of 48 mm. SEM micrographs of wall thickness and cross-sectioned beads were obtained by cutting through the dry cellular solid with a razor blade and exposing the internal surface features. The beads were glued to a polypropylene stub and gold-coated (150-200 Å) in a Polaron 5150 sputter coater (Polaron Equipment LTD., Holywall Industrial Estate Watford, Hertfordshire, England).

Electron micrographs were scanned (Hewlett Packard scanner, version 3.02, model 5300C) and analyzed using Image Pro Plus (version 3.0.01.00, Media Cybernetics, L.P.). This program determines the thickness of the marked wall measured in pixels, and translates this into metric units. Freeze-dried beads that were made from alginate (with and without *P. agglomerans*), alginate-chitin, alginate-bentonite, alginate-kaolin, alginate-glycerol, alginate-glycerol-chitin, alginate-glycerol-bentonite and alginate-glycerol-kaolin solutions containing bacteria were examined for their wall thickness.

Mechanical properties and estimated porosity: Mechanical properties of the beads were determined by uniaxial compression between lubricated plates to ~80% deformation with an Instron universal testing machine (UTM), model 5544 (Instron Co., Canton, Mass.) with a dedicated Instron card for 5544 series. 'Merlin' software bought from the Instron Company performed data acquisition and conversion of the UTM's continuous voltage vs. time output into digitized force-deformation, force-time, stress-strain or stress-time values with any desired definition of stress and strain. Since the beads' cross-sectional area remained almost unchanged even after being compressed to large deformation, an engineering stress-strain relationship could legitimately be used. The engineering stress and strain were defined, respectively, as:

$$\sigma = F/A_0 \tag{1}$$

$$\epsilon_E = \Delta H / H_0 \tag{2}$$

where $F$ is the force, $A_0$ and $H_0$ the bead's initial area and height, respectively, and $\Delta H$ the absolute deformation.

The individual relationship for freeze-dried beads could be fitted to a compressibility model previously developed for the sigmoid stress/strain relationship of cellular solids:

$$\sigma = (C_1 \cdot \epsilon_E)/[(1 + C_2 \cdot \epsilon_E) \cdot (C_3 - \epsilon_E)] \tag{3}$$

where $\sigma$=stress, $\epsilon_E$ is the engineering strain and $C_1, C_2, C_3$ are constants. The value of $C_3$ was calculated by non-linear regression. From that value, the porosity values of the freeze-dried beads were estimated using the formula:

$$\epsilon_D = 1 - 1.4(\rho/\rho s) \tag{4}$$

where $(\rho/\rho s)$ is the bulk density divided by the solid density. The densification strain $(\epsilon_D)$ was derived from the $C_3$ value, and the magnitude of the relative density $(\rho/\rho s)$ could then be estimated. Porosity was calculated by subtracting the calculated relative density from 1 and converting to a percentage.

Statistical analysis: Results represent the average of three independent experiments. Statistical analyses were conducted with JMP software, including ANOVA and the Tukey-Kramer Honestly Significant Difference Method for comparisons of means. A P value $\leq 0.05$ was considered significant.

Resistance of Microorganisms in Hydrocolloid Gels to Ultraviolet Irradiation

*T. harzianum* spores and *P. agglomerates* cells immobilized in dried alginate-glycerol beads or suspended in water were exposed to UVC radiation. Minor temperature changes (with respect to microorganism temperature optima) were detected during the UVC radiation. The maximal elevation in temperature was 8° C., and the highest temperature was 30° C. No significant differences in the temperature within and on the surface of the irradiated dried bead (cellular solid) were observed.

Figure 2:
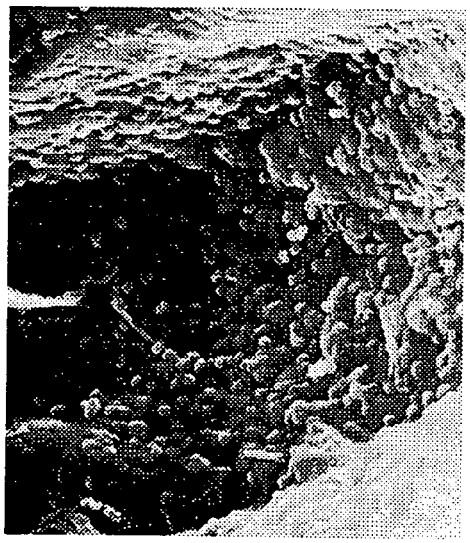
FIG. 2 shows the presence of *Trichoderma harzianum* spores within and on the inner surfaces of freeze-dried alginate beads.

SEM was performed to observe spore and bacterial distribution in the dried alginate beads. The immobilized inocula were entrapped in the dried matrix, although some microorganisms could also be found free on the surface (FIGS. 1 & 2).

Figure 3:
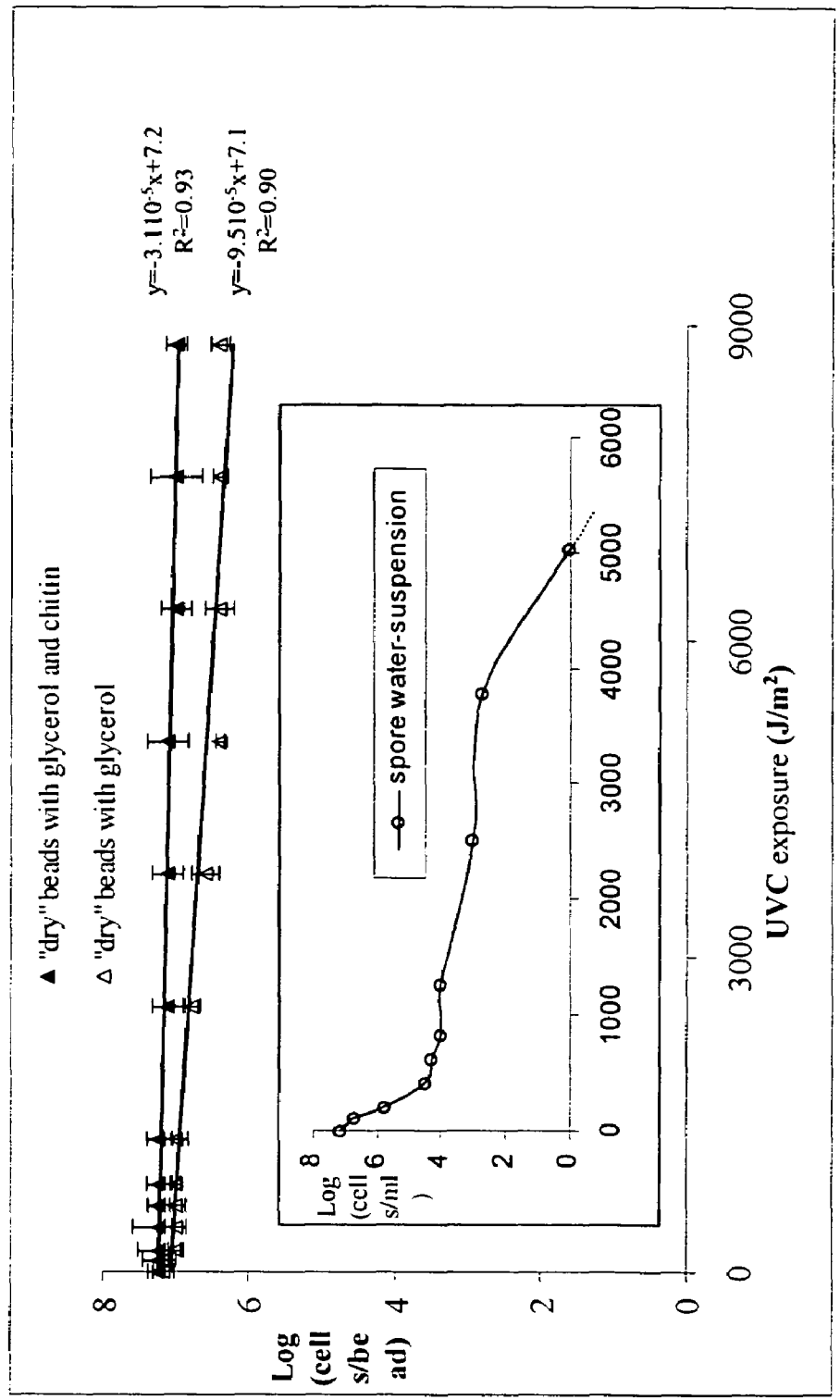
FIG. 3 demonstrates the survival of *Trichoderma harzianum* suspended in water or entrapped in freeze-dried alginate beads under UV radiation. Dashed line (inset) indicating no surviving cells below the graph values.
Figure 4:
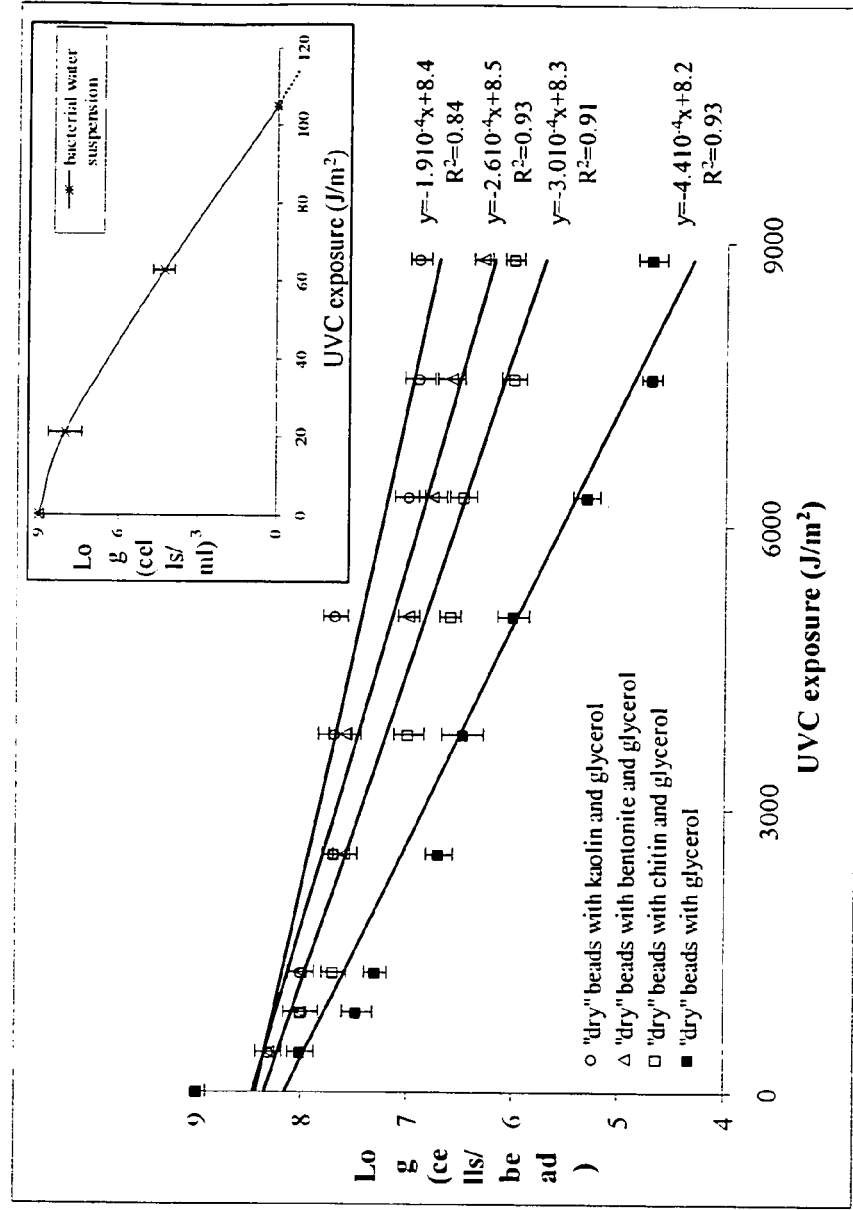
FIG. 4 demonstrates the survival of *Pantoae agglomerans* entrapped in freeze-dried beads under UV radiation. Dashed line (inset) indicating no surviving cells below the graph values.

Viability of fungal spores suspended in water was gradually reduced until no colony formation was observed after 4 h of exposure (exposure of 5040 J/m$^2$, FIG. 3 inset). However, the immobilized spore population decreased by only one order of magnitude after an exposure of 8820 J/m$^2$ (equivalent to 7 h of exposure) (FIG. 3). Improved spore survival was achieved by adding colloidal chitin to the alginate solution. The relative efficiency of killing was evaluated by linear regression analysis performed for the fungal spores included within the different beads. For the dried beads with the glycerol and glycerol with chitin, the observed slopes and the squared regression coefficients ($R^2$) were $-1 \times 10^{-4}$, $-3 \times 10^{-5}$ m$^2$/J and 0.90 and 0.93, respectively. Since the slopes were statistically different, it was concluded that chitin addition to the bead composition gives the spores better survival prospects over beads that are composed of only the water-soluble polymer with glycerol.

The control (microorganisms suspended in water) was chosen in accordance with Elcin (13) and Elcin & Oktemer (14). Since UVC exposure destroyed the entire spore population, there is more than one kinetics of death reduction at work (thus no linear regression was performed), probably because the population consists of several subpopulations, each with its own inactivation kinetics. Moreover, the inactivation time varies to some extent for each microorganism in the population, even if the population is pure. There is thus biological variation, or in other wards, heterogeneity between cells in a population of same microorganisms.

The Gram-negative, non-spore forming bacterium *P. agglomerans* was then examined. Bacterial survival in the beads decreased as the exposure to UV increased; it was however, much higher than the survival of the same microorganism suspended in water (control). Free-cell viability decreased by 90% in the first 60 s of the experiment (21 J/$m^2$) and no viable bacteria remained after 5 min of exposure (105 J/$m^2$, inset FIG. 4). In comparison, longer UVC exposure was necessary to reduce the population of bacteria immobilized in dried alginate-glycerol beads (FIG. 4).

Further improvement in bacterial viability was achieved by adding fillers (i.e. chitin, bentonite and kaolin) to the alginate-glycerol beads. The relative efficiency of killing was evaluated (FIG. 4) by linear regression analysis of log (cells/bead)

vs. UVC exposure performed for the bacteria included within the different beads. For the dried beads with glycerol (no inclusion of filler), glycerol and chitin, glycerol and bentonite, and glycerol and kaolin, the observed slopes were: $-4.4 \times 10^{-4}$, $-3.0 \times 10^{-4}$, $-2.6 \times 10^{-4}$ and $-1.9 \times 10^{-4}$ m$^2$/J, respectively, with $R^2$ of 0.93, 0.91, 0.93 and 0.84, respectively. All the slopes were differed statistically in their values and thus they could be used to distinguish between the survival prospects of the bacteria, possibly gained from the different contents of these beads. Immobilization of bacteria in alginate-glycerol-kaolin beads resulted in the highest survival during UVC exposure.

UVC Transmission of the Freeze-Dried Alginate Matrices

Since the immobilization of biocontrol agents in dried alginate beads afforded significant protection against UVC toxicity, the next step was to understand the correlation between the carriers' properties and their protection capability.

To determine the transparency of the alginate matrices to UVC light, freeze-dried flat alginate matrices (at the same thickness as the beads' diameter) were exposed to UVC radiation and transmission was measured. Alginate matrix with no addition (control) transmitted an average of 7.23±2.15% of the radiation. Filler inclusion in the matrix significantly reduced UVC transmission: alginate-kaolin, alginate-bentonite and alginate-chitin transmitted an average of 0.15±0.11%, 0.38±0.32% and 3.36±1.64%, respectively. The considerable fluctuations in these results are a consequence of the problematic cutting of these brittle cellular solids to a longitudinally uniform thickness. There was no observable advantage to adding glycerol to the formulation, probably because glycerol is transparent to UVC wavelengths.

Freeze-Dried Alginate Bead Wall Thickness

Figure 5:
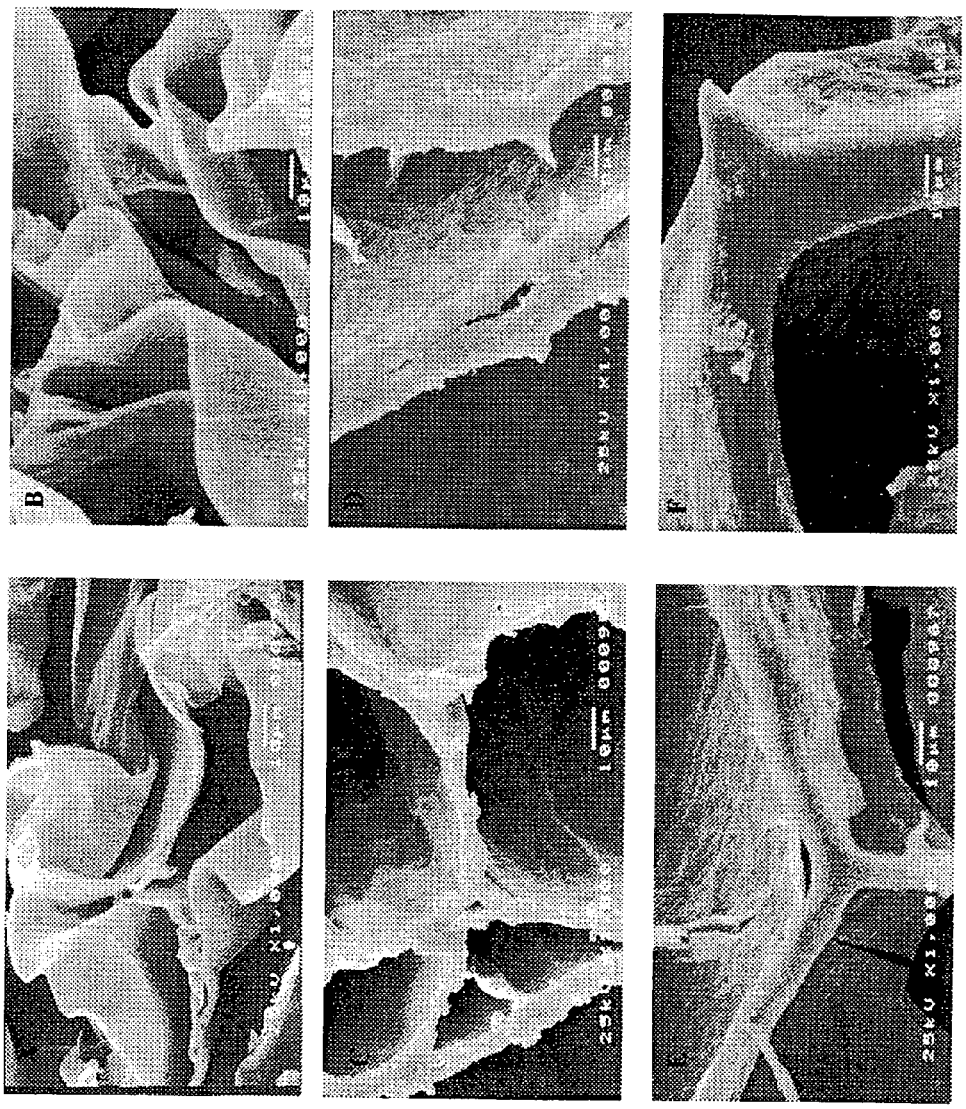
FIG. 5 shows SEM of typical freeze-dried alginate beads walls. A: Control (dry bead without bacteria). B: Dry bead. C: Dry bead with glycerol. D: Dry bead with bentonite and glycerol. E: Dry bead with chitin and glycerol. F: Dry bead with kaolin and glycerol. Preparations B to F include entrapped bacteria.

To understand the connection between bead wall thickness and protection against UVC, the wall thickness of cross-sectioned freeze-dried alginate beads was measured. The average wall thickness of alginate beads (control) was 1.47 μm, and the addition of bacteria did not produce significant thickening (Table 1, FIG. 5). Addition of glycerol, chitin, bentonite or kaolin to the beads increased bead thickness ~1.5- to 3-fold. Beads entrapping glycerol and a filler had a significantly thicker wall, with alginate-glycerol-kaolin beads having the thickest walls (11.43 μm) (Table 1).

Figure 6:
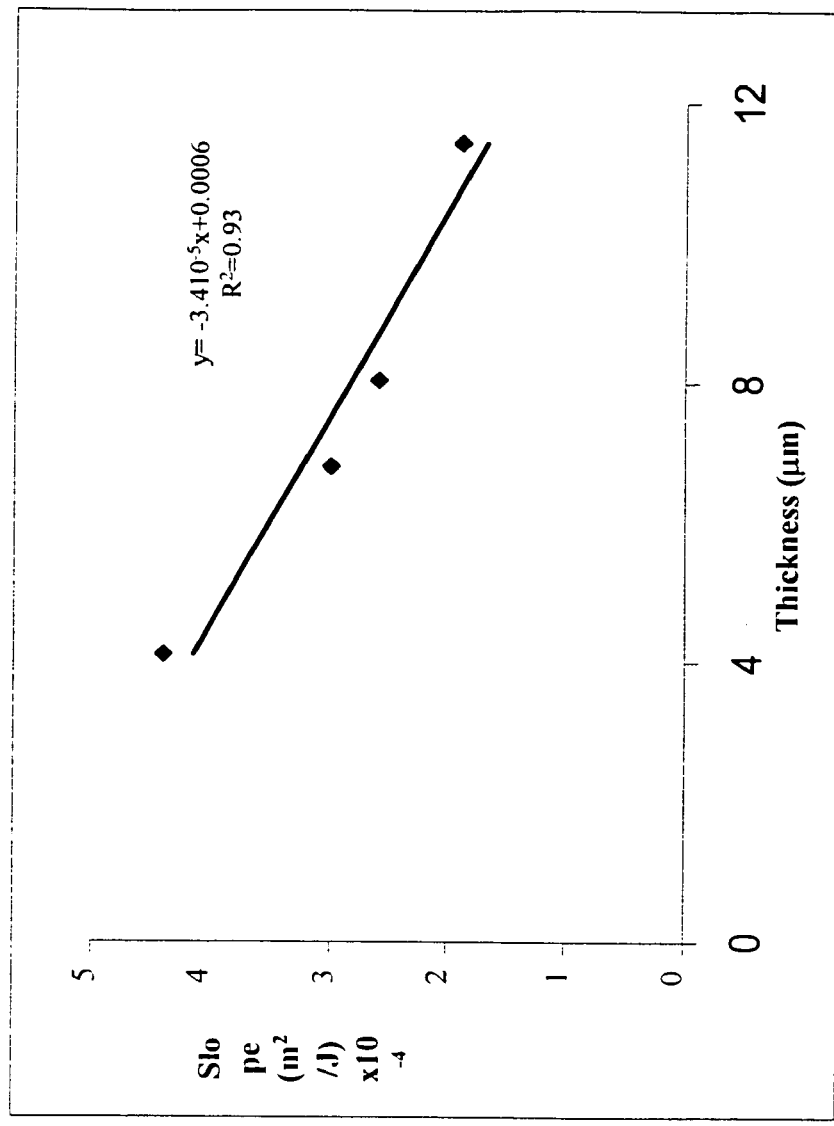
FIG. 6 shows the linear relationship between the slopes of bacterial survival curves and bead-wall thicknesses.

A linear relationship was observed between the slopes of the bacterial survival curves and wall bead thickness (FIG. 6), demonstrating an increase in survival with increasing thickness of the dried bead (cellular solid) cell walls.

Structure and Mechanical Properties of Freeze-Dried Alginate Beads

Figure 7:
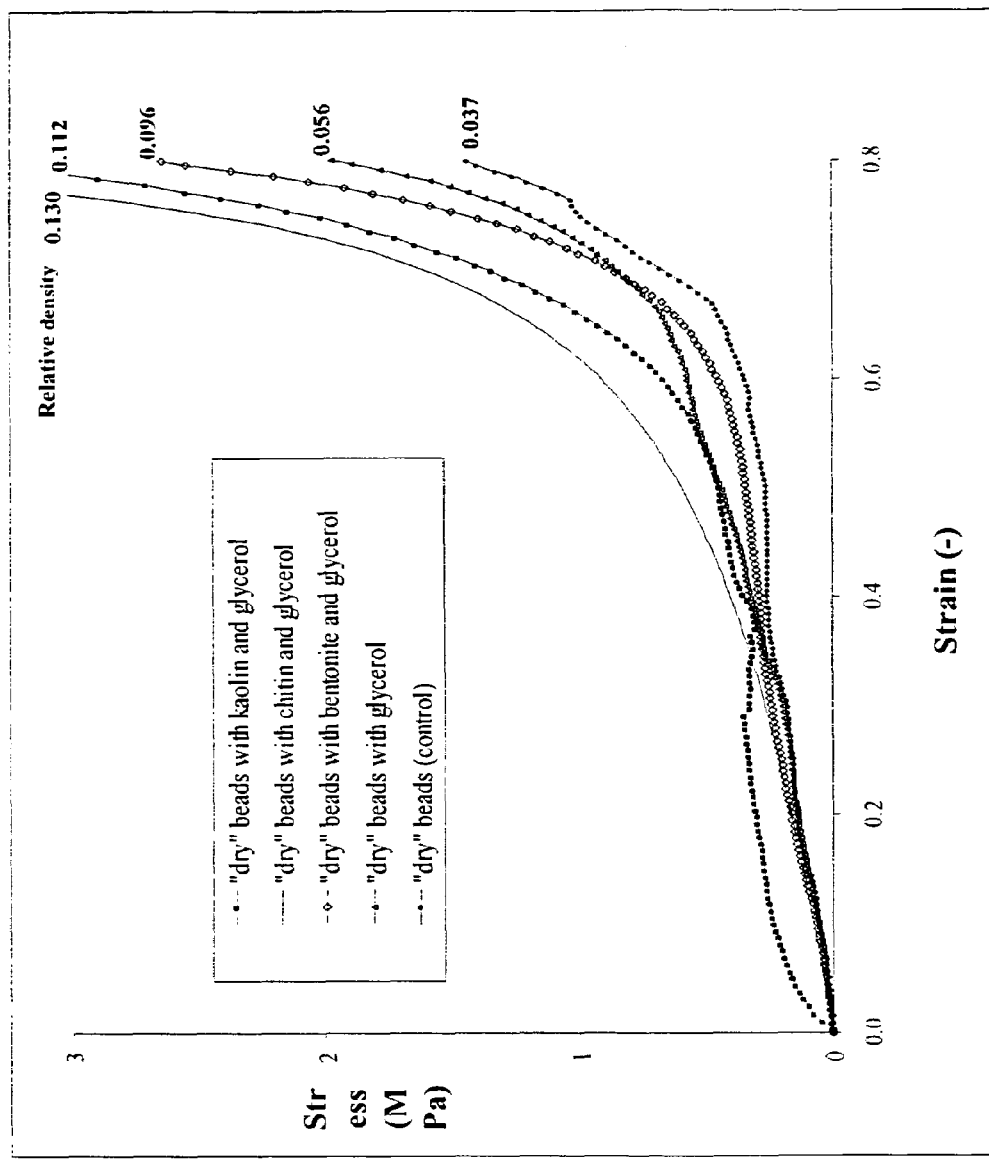
FIG. 7 shows the typical stress-strain relationship of cellular solids entrapping *Pantoae agglomerans*.

To further demonstrate the relationship between the cellular solids' (dried alginate beads') physical properties and UV protection capacity, dried alginate beads were compressed to 80% deformation in a UTM to evaluate their mechanical properties. Typical stress-strain relationships of compressed cellular solids are demonstrated in FIG. 7. Ten beads of each type were compressed. Since the results for all beads were, in fact, the same, we present only a typical curve. All beads, with or without included filler, reached densification at strains of ~95% or less. At large compressive strains, the opposing walls of the cells crush together and the cell wall material itself is compressed. When this happens, the stress-strain curve rises steeply at a limiting strain of $\epsilon_D$ (FIG. 7). For both open-cell and closed-cell foams, equation 4 holds. The dried beads without any addition, those with glycerol, bentonite and glycerol, kaolin and glycerol, and chitin and glycerol reached densification at 0.949, 0.922, 0.866, 0.843 and 0.819, respectively. From these values the porosity of the cellular alginate beads was evaluated. The porosity of the beads with no addition (control) was 96%±1. The addition of glycerol resulted in a reduction in the porosity to 94%±0.1. A further significant decrease to values of 90%±1.3, 88%±1 and 87%±1.5 was observed following the addition of bentonite, kaolin and chitin, respectively.

A descending non-significant relationship between the slopes of the bacterial survival curves and bead porosity was observed (results not shown). These results imply that in general, the higher the beads' porosity the lower the survival percentage.

Figure 8:
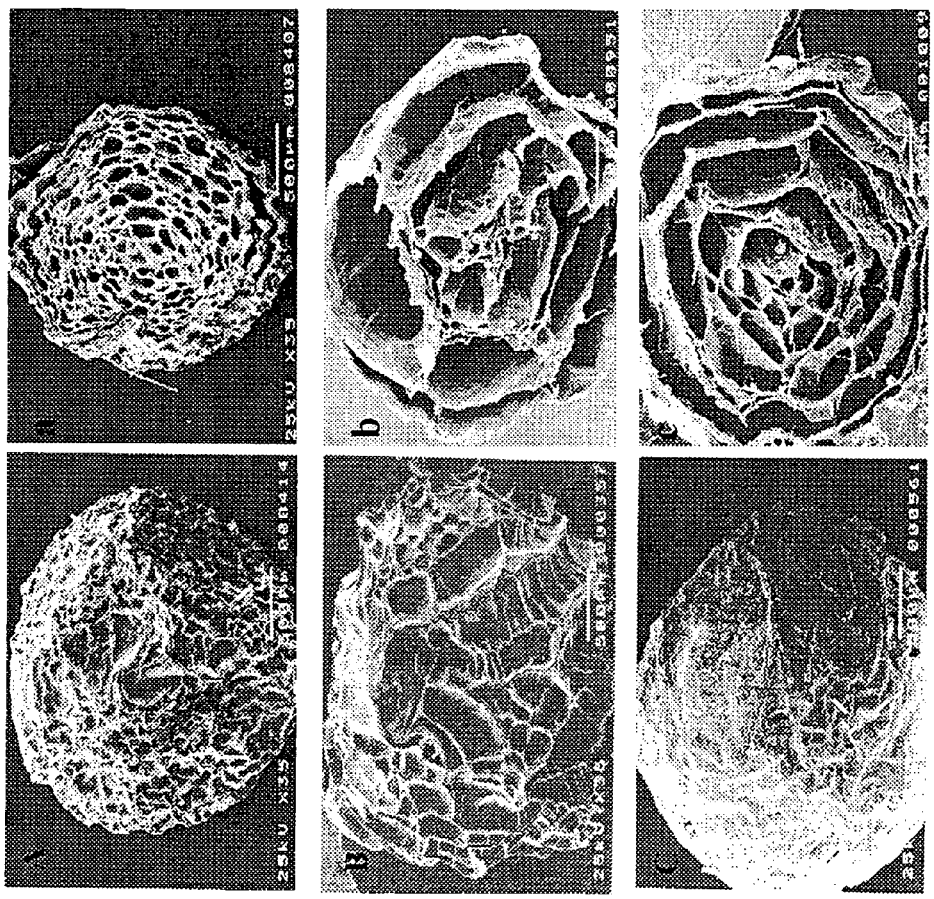
FIG. 8 shows electron micrographs of alginate (A), alginate-glycerol (B) and alginate-glycerol-chitin (C) freeze-dried beads entrapping *Pantoae agglomerans*. A served as a blank, i.e. a non-irradiated dried alginate bead a, b, c are cross sections of A, B and C, respectively.

The structure of the cellular solids entrapping the bacteria depended on their content. The addition of filler (i.e. bentonite, kaolin or chitin) to this formulation had a considerable influence on the structure of the outer surface of the dried beads. Less local shrinkage and folds may have been due to stabilization of the structure by the filler particles (FIG. 8 A-C). The inclusion of glycerol in the alginate solution designed for the production of the dried beads produced different inner bead structures (FIG. 8a-c). Without glycerol inclusion (FIG. 8a), i.e. a bead based on alginate, the proportion of pores with minimal surface area was the greatest. The presence of glycerol in the dried products (FIGS. 8b-c) resulted in changes in the pore distribution of these moieties, suggesting that the proportion of pores with increased area shifts to a population with both very small and very large pores. These results demonstrate that the inclusion of glycerol and fillers within the composition controls the structure of the cellular solids, in addition to influencing their pore-size distribution and porosity.

TABLE 1

Freeze-dried alginate bead wall thickness (μm)

| Type of inclusion in the beads | Average | SD |
|---|---|---|
| Control | 1.47$^a$ | 0.35 |
| Bacteria | 1.55$^a$ | 0.47 |
| Chitin | 2.30$^b$ | 0.86 |
| Bentonite | 3.23$^c$ | 1.22 |
| Kaolin | 3.52$^c$ | 0.85 |
| Glycerol | 4.12$^c$ | 1.50 |
| Chitin and glycerol | 6.80$^d$ | 1.97 |
| Bentonite and glycerol | 8.03$^d$ | 3.37 |
| Kaolin and glycerol | 11.43$^e$ | 2.81 |

In each case the data are derived from the analysis of 10 beads.

Values with different letter subscripts are significantly different at $P \leq 0.05$.

Example 2

In Vitro Antifungal Activity Against the Plant Pathogenic Fungus R. solani Using P. agglomerans Entrapped in Dried Alginate Beads Materials and Methods Alginate-glycerol beads, with or without chitin, and before and after freeze-dehydration, entrapping P. agglomerans (10$^7$ cells/bead), were seeded at two corners of a PDA plate (9 cm) and incubated at 28° C. for 5 days. A 5-mm-diameter agar disk from the actively growing pathogenic fungal culture R. solani was then placed at the center of the PDA plate and the plates were incubated at 28° C. until mycelium growing on a control plate (containing beads without bacteria in the corners) covered the whole plate area. The extent of mycelial growth on plates containing beads was then estimated.

Results

Figure 9:
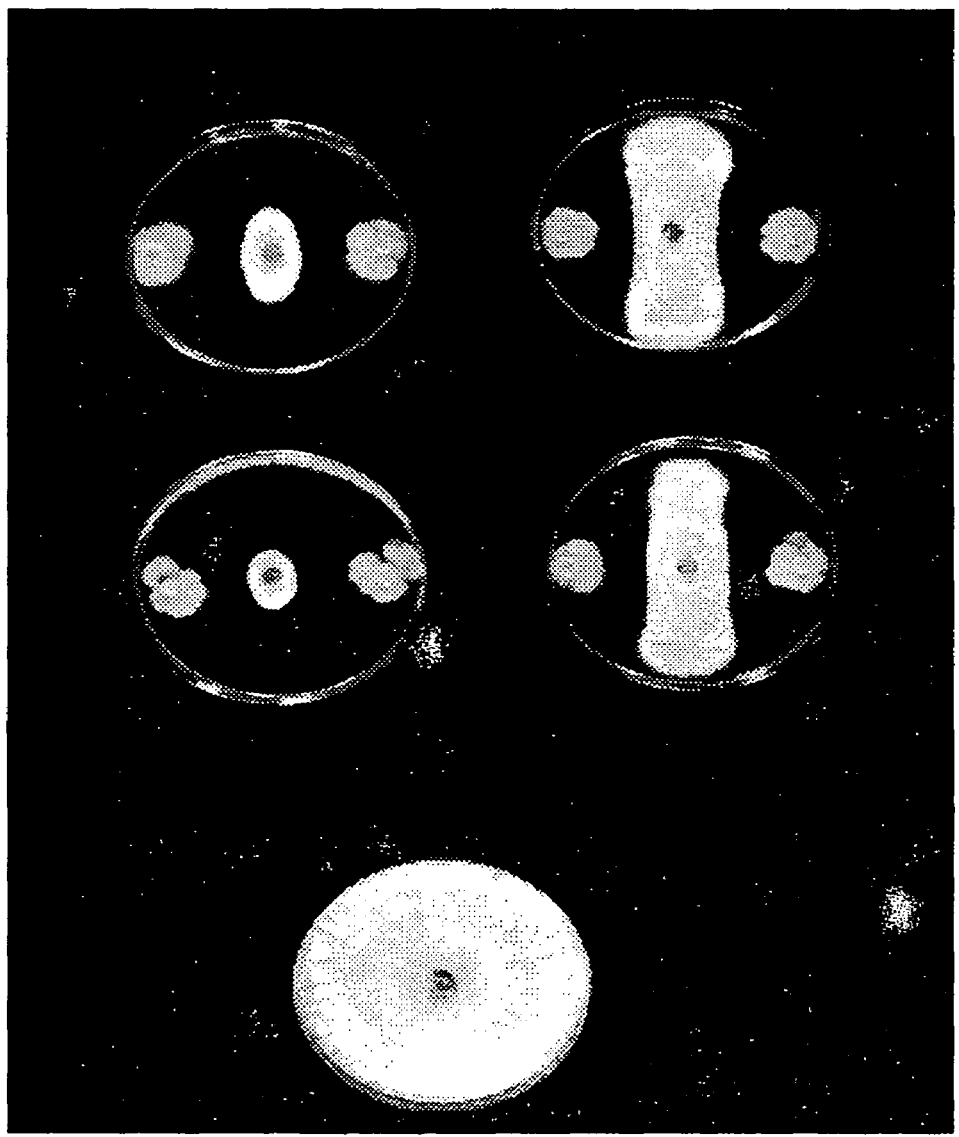
FIG. 9 demonstrates the antagonistic activity in vitro of immobilized *Pantoae agglomerans* in gel and freeze-dried alginate-glycerol beads (with or without chitin) against *Rhizoctonia solani*. A: dried beads with chitin; B: dried beads without chitin; C: gel beads with chitin; D: gel beads without chitin; E: control (without immobilized *P. agglomerans*).

As described, three different fillers (kaolin, bentonite and chitin) were used. Only one of them, chitin, had proven biological control activity (15). Therefore, the antifungal activity of the immobilized biocontrol agent *P. agglomerans* in dried alginate beads (in comparison to gel beads) was examined including chitin. This bacterium, entrapped in the dried beads, suppressed the growth of the plant pathogenic fungus *R. solani* more strongly than the same bacterium entrapped in the gel beads (FIG. 9). This improved antifungal activity is probably a result of the different external (surface features) and internal structures of the dried vs. non-dried gel beads.

Freeze-drying of a gel bead results in a low-density dried cellular product that is composed of many fused open and closed cells (Nussinovitch, Velez-Silvestre & Peleg, 1993). This cellular structure enables the controlled release of microbial cells or their products from the matrix (Zohar-Perez et al., 2002) and thus exhibits enhanced antagonistic activity. It is not surprising that addition of chitin to the beads' formulation resulted in improved antifungal effect in both gel and dried beads. Chitinolytic bacteria such as *P. agglomerans* can utilize chitin as the sole carbon and nitrogen source. It is also well known that chitin is an inducer of chitinolytic enzyme production by *P. agglomerans*. The latter is of particular interest in cases where immobilized chitinolytic microorganism preparations are used as biocontrol agents of plant-pathogenic fungi carrying chitin as the major structural component of their cell walls.

Example 3

Antifungal activity of *P. agglomerans* and *Serratia marcescens* entrapped in Dried Alginate Beads in Greenhouse Conditions Materials and Methods Culture medium and bacterial growth: For entrapment, the chitinolytic biocontrol agents *Serratia marcescens* and *Pantoae agglomerans* IC1270 were used. The bacteria were grown on liquid or solid (2% w/v agar) Luria broth (LB) or agar (LA) at 30° C., for 24 h with aeration, to a final concentration of ~$10^9$ cells/ml. Bacterial cells were separated by centrifugation at 4100×g in a refrigerated superspeed centrifuge (Universal 16R, Hettich, Gartenstrabe, Tuttlingen) for 15 min at 20° C. and suspended in sterile distilled water.

Preparation of the immobilization complex: Alginate (60-70 kDa, M:G 61:39, Sigma, LV, St. Louis, Mo.), was dissolved in distilled water (2% w/w). Glycerol (30% w/w, final concentration) was added to the alginate solution (2% w/w, final concentration). For the alginate-chitin bead preparation, a colloidal chitin suspension, was added to an alginate-glycerol solution to a final concentration of 1% (w/w). All mixtures were sterilized by autoclaving. *S. marcescens* or *P. agglomerans* (~$10^{11}$ cells/ml) was then added at a 1:9 volumetric ratio to alginate-glycerol or alginate-glycerol-chitin solutions. This final mixture was dripped into a 1% (w/w) sterile solution of calcium chloride and stirred for 30 min (the volumetric ratio between the alginate mixture and the calcium chloride solution was 1:100). A spontaneous cross-linking reaction produced spherical gel beads with an average diameter of about 4 mm, containing ~$10^9$ cells/bead. The beads were frozen at −80° C. for 1 h before freeze-drying, which was carried out at −50° C. at a pressure of 1.1 Pa (Martin Christ model ALFA I-5, Osterode am Harz, Germany).

Soil inoculation (for slow release experiments): 250 beads (each entrapping ~$10^9$ cells of *S. marcescens*) were mixed with 50 g of sieved (2 mm mesh) sterile Rehovot sandy loam soil (82.3% sand, 2.3% silt, 15% clay, 0.4% organic matter, pH 7.2) in sterile Petri dish (9 cm diameter) and the water content (tap water) was adjusted to 70% of the water holding capacity. Small holes were made in the dishes cover plate to ensure air exchange. Then the dished were weighted and kept at 30° C. in an incubator. Subsequently, to maintain soil humidity, the dished were weighted every 1-2 days and sterile tap water was supplemented to the soil to compensate for the amount of water lost by evaporation.

Measuring of chitinolytic activity and bacterial enumeration in soil: every ~3 days soil subsamples were collected from each dish and separated from the beads. Four soil samples (0.5 g) and 10 beads were subjected to chitinase assay and bacterial enumeration. The soil samples (immersed in sterile citrate buffer, pH 6) and the beads (immersed in 2% (w/w) sterile sodium citrate solution) were shaken (300 rpm) in sterile plastic tubes for 30 min to extracted chitinase enzymes and bacterial cells. Then, a sample of the immersion solution (of the soil and beads as well) was taken for bacterial enumeration; the released cells (from soil or beads) were immediately serially diluted, plated on LA and incubated for 24 h at 30° C. The soil sediment in the tubes was removed by centrifugation (2500 rpm, 10 min). Chitinolytic activity in the beads and soil was determined using 4-Methylumbelliferyl β-D-N,N'-diacetylchitobioside (4-MU-(GlcNAc)$_2$, Sigma). Reaction mixtures contained 170 μl soil or bead extraction, 20 μl 0.1 mg/ml BSA and 10 μl 1 mM 4-MU-(GlcNAc)$_2$. The reaction mixture (total volume 200 μl) was incubated at 37° C. for 10 min, after which reaction was stopped by adding 50 μl 0.2M Na$_2$CO$_3$. The amount of 4MU release was determined with Fluorimeter (Varian, Cary eclipse), with excitation at 360 nm and emission at 450 nm, using 4MU solution as standard. One unit of chitinase activity was defined as the amount of enzyme that liberated 1 nmole of 4MU in one hour and expressed per 1 g dry soil or per bead.

Pathogenic fungi preparation: The fungus *Pythium aphanidermatum* was grown on Petri dishes with Corn Meal Agar for 4 days at 28° C. and then each plate was grinded in an Ultra-Turrax (Janke & Kunkel, Breisgau, FRG) with 40 ml of tap water.

Greenhouse assays: Polypropylene boxes (11×9×6 cm) were two-thirds filled with Rehovot sandy loam soil (82.3% sand, 2.3% silt, 15% clay, 0.4% organic matter, pH 7.2) and 10 seeds of cucumber (*Cucumber sativus* L.) were placed in each box. On top of each seed, 2 beads entrapping *P. agglomerans* (~$10^9$ cells/bead) or 2 ml (~$10^9$ cells/ml) of bacterial solution (bacterial control), and 0.5 ml preparation of *P. aphanidematum* were sited. Germination control plants were grown in untreated soil and disease control plants were grown without addition of the biocontrol bacteria. Each treatment was tested in four replicates and experiments carried out under standard greenhouse conditions at 28-32° C. Disease incidence was determined after 12 to 14 days as the percentage of seedlings with symptoms of damping-off disease.

Efficiency of Biocontrol Using Hydrocolloid Beads Comprising Microorganisms

Figure 10:
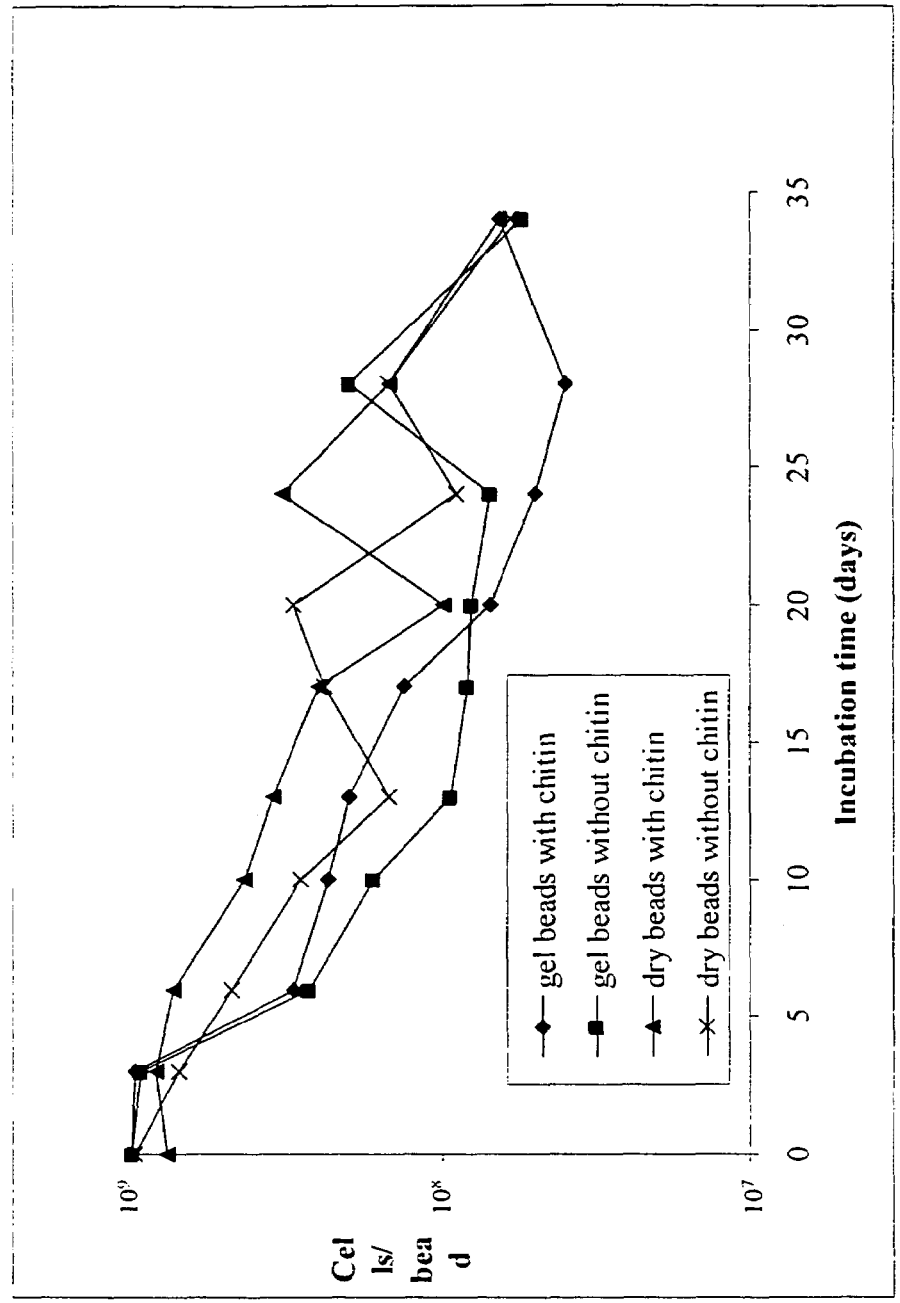
FIG. 10 shows the enumeration of bacterial cells within alginate beads incubated in soil.
Figure 11:
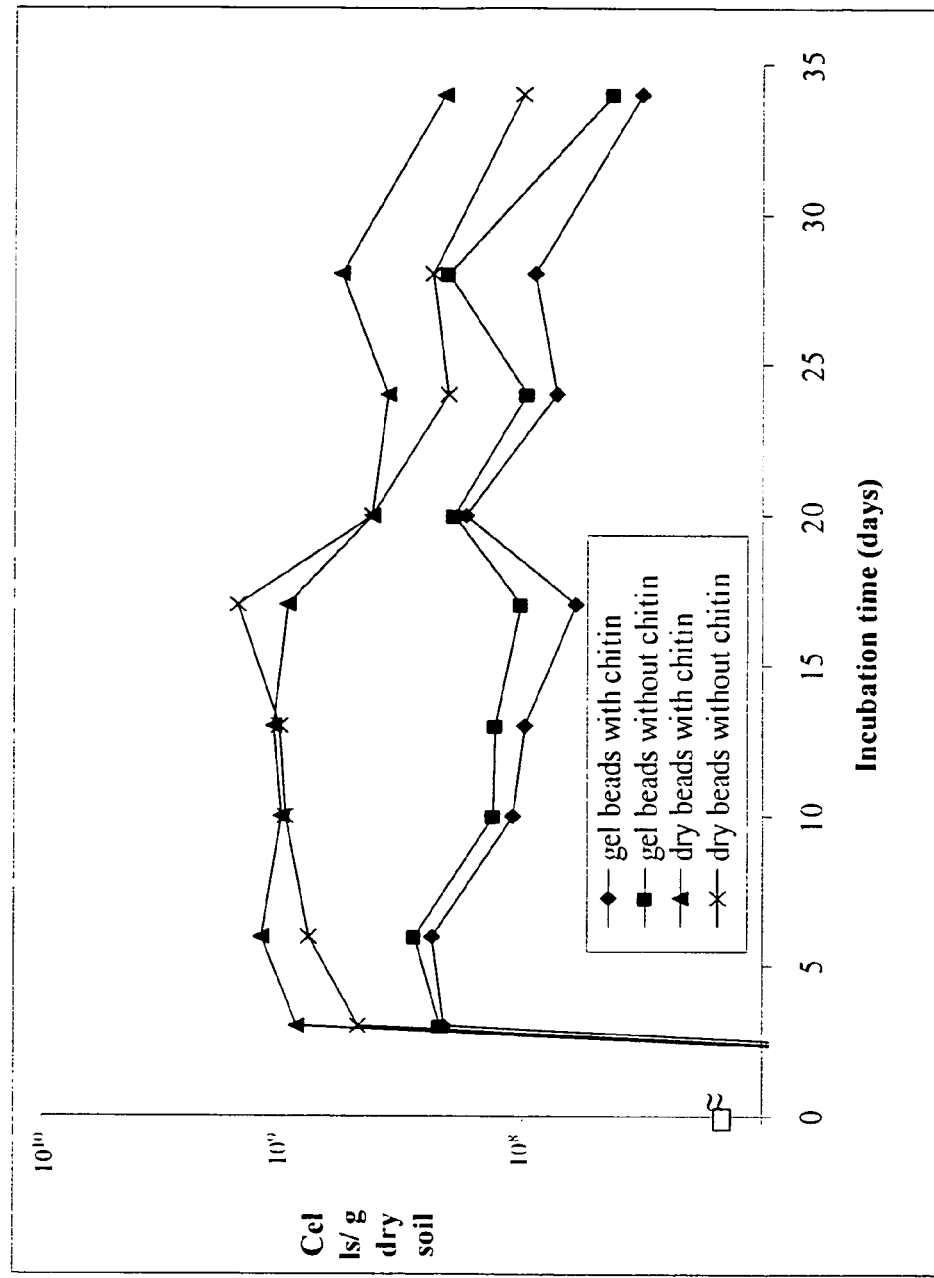
FIG. 11 shows the enumeration of bacterial cells released from alginate beads in soil.
Figure 12:
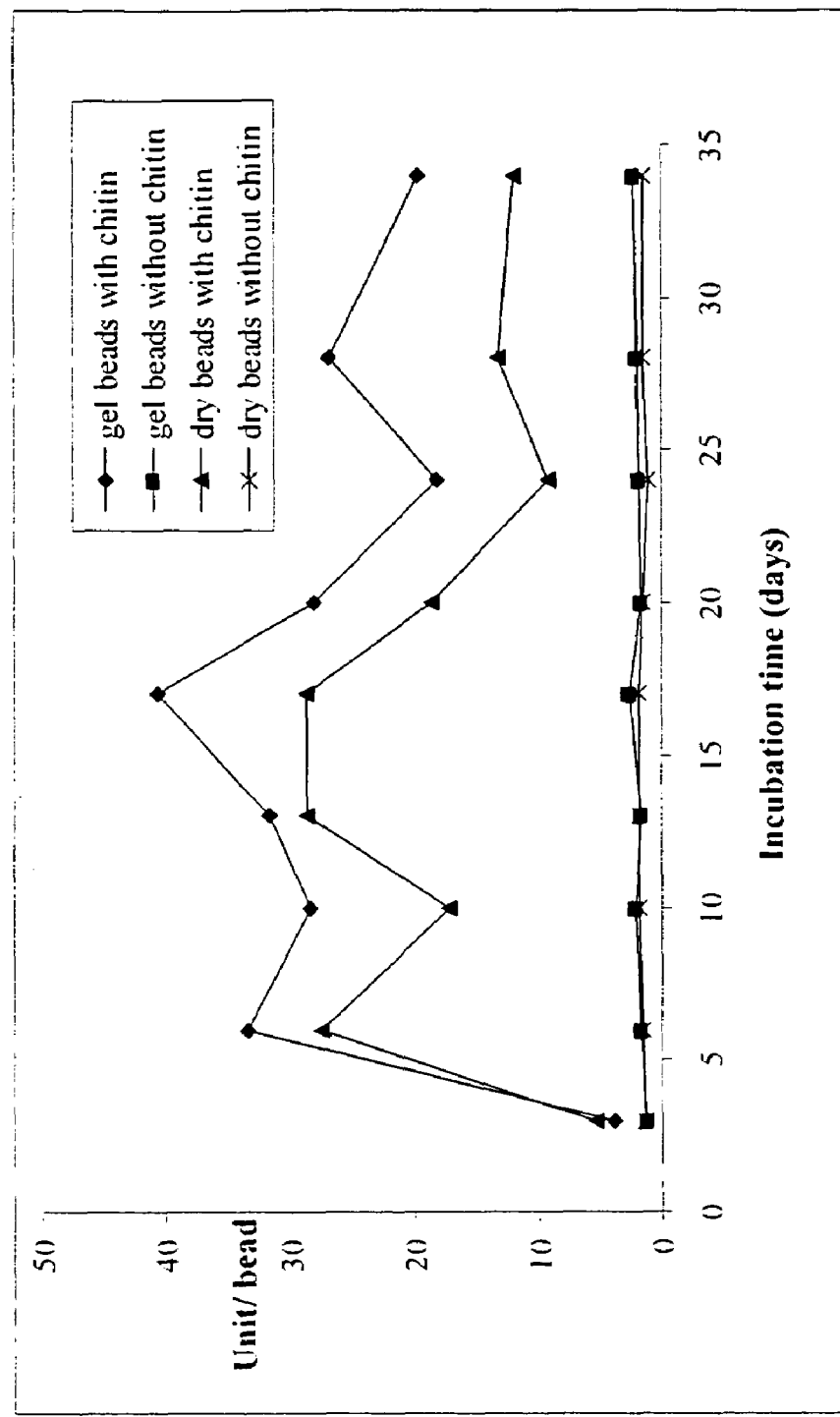
FIG. 12 shows the chitinase activity within alginate beads incubated in soil.
Figure 13:
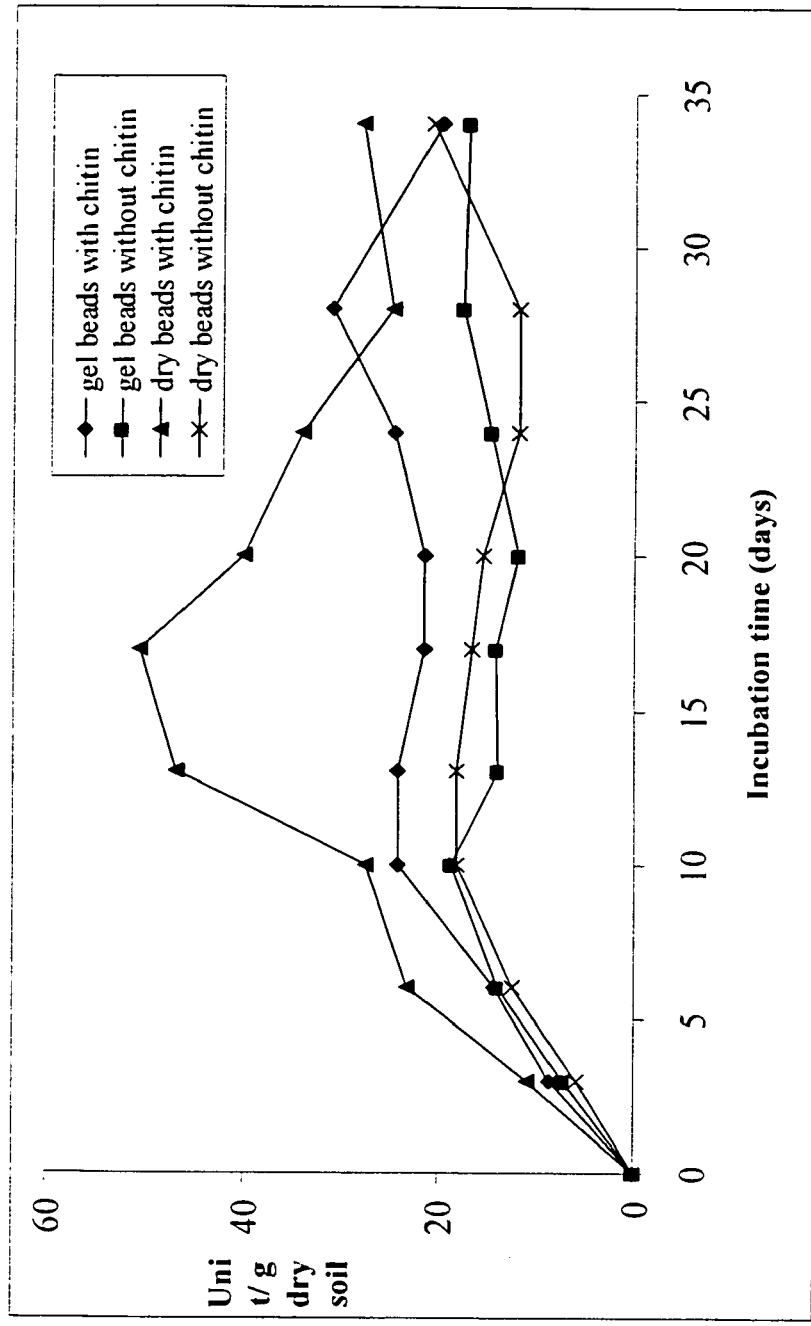
FIG. 13 shows the chitinase activity released from alginate beads in soil.
Figure 14:
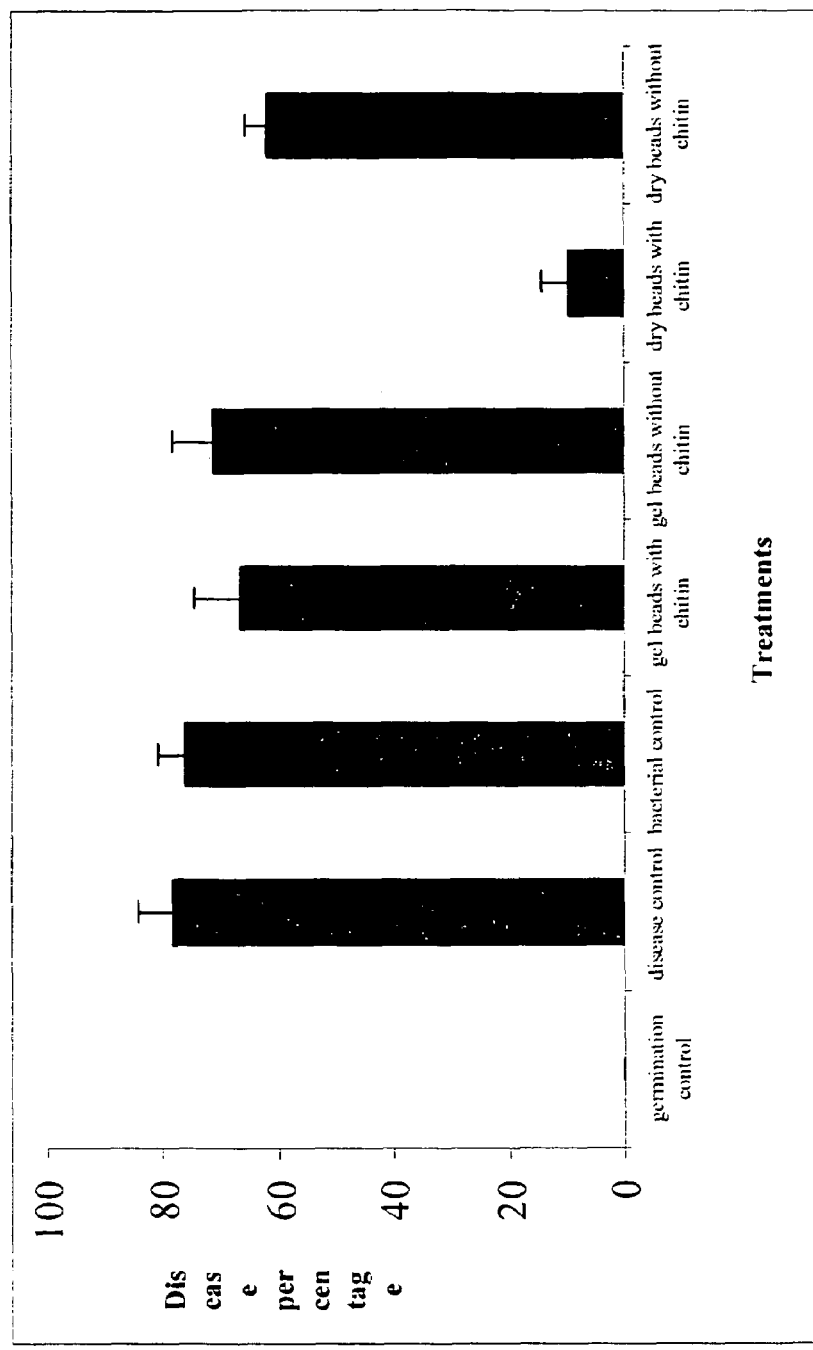
FIG. 14 demonstrates the effect of soil inoculation with antagonistic *Pantoae agglomerans* on the percentage of cucumber disease.

In order to evaluate the feasibility of the dried alginate beads as a carrier for biocontrol microorganisms the following analysis was carried out. FIG. 10 represents the enumeration of bacterial cells within alginate beads incubated in soil for up to 35 days. As revealed from FIG. 10, no significant difference was found in the number of bacterial cells within the beads with or without chitin. Furthermore, dry beads tend to be preferred as compared to gel beads. FIG. 11 demonstrates the number of bacterial cells released from the alginate beads to the soil. As revealed from FIG. 11, the number of bacterial cells released from the alginate beads to the soil is higher in the dry beads as compared to the gel beads. Furthermore, as revealed from FIG. 12, the chitinase activity within alginate beads when chitin is incorporated into the beads is higher in the dry beads as compared to the gel beads. FIG. 13 demonstrates that chitinase diffusion to the soil is higher when the beads are dried as compared to gel beads. The advantage of using bacterial cells entrapped in dry alginate beads in reducing a cucumber disease is demonstrated in FIG. 14. As revealed from FIG. 14, *P. agglomerans* entrapped in dry beads with chitin demonstrated dramatic effect on the percentage of cucumber disease in greenhouse conditions.

It will be appreciated by a person skilled in the art that the present invention is not limited by what has been particularly shown and described hereinabove. Rather, the scope of the invention is defined by the claims that follow.

REFERENCES

1. Y. Bashan. Inoculants of plant growth-promoting bacteria for use in agriculture. Biotechnol. Adv. 16, 729-70 (1998).
2. C. Cokmuis, A. HakkiSayar, S. C. Sacilik, O. Osmanaaolu and I. Berber, Effects of UV-light on *Bacillus sphaericus* and its protection by chemicals. J. Basic Microbiol. 40(4), 215-221 (2000).
3. G. D. Inglis, M. S. Goettel and D. L. Johnson, Influence of ultraviolet light protectants on persistence of the entomopathogenic fungus, *Beauveria bassiana*. Biol. Control 5(4), 581-590 (1995).
4. L. Chernin, A. Brandis, Z. Ismailov and I. Chet, Pyrrolnitrin production by an *Enterobacter agglomerans* strain with a broad spectrum of antagonistic activity towards fungal and bacterial plant pathogens. Curr. Microbiol. 32, 208-212 (1996).
5. K. H. Van Pee and J. M. Ligon, Biosynthesis of pyrrolnitrin and other phenylpyrrole derivatives by bacteria. Nat. Prod. Rep. 17, 157-64 (2000).
6. A. Nussinovitch, R. Velez-Silvestre and M. Peleg, Compressive characteristics of freeze-dried agar and alginate gel sponges. Biotechnol. Prog. 9(1), 101-104 (1993).
7. Y. Tal, J. van Rijn, and A. Nussinovitch, Improvement of structural and mechanical properties of denitrifying alginate beads by freeze-drying. Biotechnol. Prog. 13, 788-93 (1997).
8. Y. Tal, J. van Rijn and A. Nussinovitch, Improvement of mechanical and biological properties of freeze-dried denitrifying alginate beads by using starch as a filler and carbon source. Appl. Microbiol. Biotechnol. 51, 773-779 (1999).
9. C. Zohar-Perez, E. Ritte, L. Chernin, I. Chet and A. Nussinovitch, Preservation of chitinolytic Pantoae agglomerans in a viable form by cellular dried alginate-based carriers. Biotechnol. Prog. 18, 1133-1140 (2002).
10. L. Chernin, Z. Ismailov, S. Haran and I. Chet, Chitinolytic *Enterobacter agglomerans* antagonistic fungal plant pathogens. Appl. Environ. Microbiol. 5, 1720-1726 (1995).
11. Y. Elad, I. Chet and Y. Henis, Degradation of plant pathogenic fungi by *Trichoderma harzianum*, Can. J. Microbiol. 28, 719-725 (1982).
12. R. Rodriguez-Kabana, G. Godoy, G. Morgan-Jones and R. A Shelby, The determination of soil chitinase activity: conditions for assay and ecological studies. Plant Soil 75, 95-106 (1983).
13. Y. M. Elcin, *Bacillus sphaericus* 2362-calcium alginate microcapsules for mosquito control. Enzyme Microbiol. Technol. 17, 587-591 (1995).
14. Y. M. Elcin and A. Oktemer, Larvicidal and sporal behaviour of *Bacillus sphaericus* 2362 in carrageenan microcapsules. J. Control Release 33(2), 245-251 (1995).
15. Chet, I. (1987) *Trichoderma*—application, mode of action and potential as a biocontrol agent of soilborne plant pathogenic fungi. In Innovative approaches to plant disease control (pp. 137-60). Chet, I. (Ed.). New York: John Wiley & Sons.

What is claimed is:

1. Solid porous cellular hydrocolloid carriers comprising porous freeze-dried hydrocolloid beads that include viable microorganisms entrapped therein, wherein the hydrocolloid is an alginate, agarose, Low Methoxy Pectin (LMP), polyvinyl alcohol (PVA), Carrageenan or xanthan plus locust bean gum (LBG); and wherein the freeze-dried beads have diameters ranging from 50 microns to 500 microns; have a residual moisture of no more than 12%, and include a cryoprotectant comprising glycerol in an amount of 10 to 50% by weight of the hydrocolloid, wherein a not less than 50% to 95% of the microorganisms are viable both during freeze drying and after 12 to 36 months of storage as a dried solid at temperatures at or below minus 18° C.

2. The solid cellular carriers according to claim 1, wherein exposure to moisture induces growth of the entrapped microorganism within the hydrocolloid beads.

3. The solid cellular carriers according to claim 1, wherein exposure to moisture induces extended release into the environment of either the entrapped microorganisms or active products produced by the microorganisms.

4. The solid cellular carriers of claim 1, wherein the hydrocolloid is alginate.

5. The solid cellular carriers of claim 1, wherein the hydrocolloid carriers are biodegradable.

6. The solid cellular carriers of claim 1, wherein the microorganisms are bacteria or fungi capable of controlling plant pathogens.

7. The solid cellular carriers of claim 6, wherein the microorganisms are fungi selected from the group consisting of *Trichoderma harzianum, Trichoderma lignorum* and *Trichoderma viride.*

8. The solid cellular carriers of claim 6, wherein the microorganisms are bacteria capable of controlling plant pathogens.

9. The solid cellular carriers of claim 8, wherein the bacteria are selected from the group consisting of *Pantoae agglomerans, Serratia marcescens, Bacillus* Spp., *Enterobacter* Spp., *Azotobacter, Azospirillum* and *Pseudomonas.*

10. The solid cellular carriers of claim 3, wherein the active products produced by the microorganisms are enzymes or antibiotics selected from the group consisting of chitinase, gluconases, proteases, pyrolnitrin, pyrolniteorin, phenazines, DAPG (2,4,diacetylfluoroglucinol), ferrichrome A and desferrioxamine B.

11. The solid cellular carriers of claim 1, further comprising one or more of nutrients, fillers, agents for controlling the porosity of the carriers, agents that prevent damage to the viable microorganisms during freezing, or agents that control cell wall thickness.

12. The solid cellular carriers of claim 11, wherein the nutrients or fillers are selected from the group consisting of chitin, pectin, cellulose, lignin, bentonite, kaolin, starch, glycerol and lowfat milk.

13. The solid cellular carriers of claim 8, wherein the plant pathogens are selected from the group consisting of *Pythium aphanidermatum, S. scabies, Verticillium dahliae, Verticillium albo-atrum, Fusarium solani, Rhizoctonia solani, Cylindrocladium floridanum, Clavibacter michiganense* subsp. *sepidonicum, Phytophthora megasperma* pv. *glycinea* race 1, *Pythium* spp., *Septoria* spp. and *Sclerotinia*.

14. The solid cellular carriers of claim 1, wherein the carriers have a bead wall thickness of about 1.55 micrometers to about 11.43 micrometers.

15. A method of producing the cellular solid carriers according to claim 1 which comprises:
mixing a hydrocolloid solution with viable microorganisms, wherein the hydrocolloid is an alginate, agarose, Low Methoxy Pectin (LMP), polyvinyl alcohol (PVA), Carrageenan or xanthan plus locust bean gum (LBG);
adding a cryoprotectant comprising glycerol in an amount of 10 to 50% by weight of the hydrocolloid to the hydrocolloid solution and microorganisms to form a mixture; and
freeze drying the mixture under conditions which preserve the porosity of the mixture, thereby forming freeze-dried cellular solid hydrocolloid beads having diameters ranging from 50 microns to 500 microns and a residual moisture of no more than 12%, with the beads comprising viable microorganisms entrapped in the porosity of the beads, wherein not less than 50% to 95% of the microorganisms are viable both during freeze drying and after 12 to 36 months of storage as a dried solid at temperatures at or below minus 18° C.

16. The method of claim 15, which further comprises adding to the mixture one of more of nutrients, fillers, agents for controlling the porosity of the beads, agents that prevent damage to the viable microorganisms during freezing, or agents that control cell wall thickness.

17. The method of claim 16, wherein the nutrients or fillers are selected from the group consisting of chitin, pectin, cellulose, lignin, bentonite, kaolin, starch, and lowfat milk.

18. A method for controlling plant pathogens in an agricultural crop which comprises: applying the solid porous cellular carriers according to claim 1 to an entity selected from seeds, seedlings or plants of an agricultural crop wherein the microorganisms or active products produced by the microorganisms are released from the beads to effectively control plant pathogens.

19. The method of claim 18, which further comprises contacting the beads with moisture to induce extended release into the surrounding environment of either the entrapped microorganisms or active products produced by the microorganisms.

20. The method of claim 19, wherein said hydrocolloid is alginate.

21. The method of claim 18, wherein the microorganisms are bacteria or fungi capable of controlling plant pathogens.

22. The method of claim 21, wherein said fungi are selected from the group consisting of *Trichoderma harzianum, Trichoderma lignorum* and *Trichoderma viride.*

23. The method of claim 21, wherein said bacteria are selected from the group consisting of *Pantoae agglomerans, Serratia marcescens, Bacillus* Spp., *Enterobacter* Spp., *Azotobacter, Azospirillum* and *Pseudomonas.*

24. The method of claim 18, wherein the active products produced by the microorganisms are enzymes or antibiotics selected from the group consisting of chitinase, gluconases, proteases, pyrolnitrin, pyrolniteorin, phenazines, DAPG (2,4, diacetylfluoroglucinol), ferrichrome A and desferrioxamine B.

25. Solid porous cellular hydrocolloid carriers comprising porous freeze-dried hydrocolloid beads that include viable microorganisms entrapped therein, wherein the hydrocolloid is an alginate, agarose, Low Methoxy Pectin (LMP), polyvinyl alcohol (PVA), Carrageenan or xanthan plus locust bean gum (LBG); and wherein the freeze-dried beads have diameters ranging from 50 microns to 500 microns; have a residual moisture of no more than 12%, include a cryoprotectant comprising glycerol in an amount of 10 to 50% by weight of the hydrocolloid, and include one or more of nutrients or fillers selected from the group consisting of chitin, pectin, cellulose, lignin, bentonite, kaolin, starch, glycerol and lowfat milk, wherein not less than 50% to 95% of the microorganisms are viable both during freeze drying and after 12 to 36 months of storage as a dried solid at temperatures at or below minus 18° C.

26. A method for controlling plant pathogens in an agricultural crop which comprises: applying the solid porous cellular carriers according to claim 25 to an entity selected from seeds, seedlings or plants of an agricultural crop wherein the microorganisms or active products produced by the microorganisms are released from the beads to effectively control plant pathogens.

27. A method of producing the cellular solid carriers according to claim 25 which comprises:

mixing a hydrocolloid solution with viable microorganisms, wherein the hydrocolloid is an alginate, agarose, Low Methoxy Pectin (LMP), polyvinyl alcohol (PVA), Carrageenan or xanthan plus locust bean gum (LBG);

adding a cryoprotectant comprising glycerol in an amount of 10 to 50% by weight of the hydrocolloid to the hydrocolloid solution and microorganisms to form a mixture;

including in the mixture one or more of nutrients or fillers selected from the group consisting of chitin, pectin, cellulose, lignin, bentonite, kaolin, starch, glycerol and lowfat; and freeze drying the mixture under conditions which preserve the porosity of the mixture, thereby forming freeze-dried cellular solid hydrocolloid beads having diameters ranging from 50 microns to 500 microns and a residual moisture of no more than 12%, with the beads comprising viable microorganisms entrapped in the porosity of the beads, wherein not less than 50% to 95% of the microorganisms are viable both during freeze drying and after 12 to 36 months of storage as a dried solid at temperatures at or below minus 18° C.

* * * * *

UNITED STATES PATENT AND TRADEMARK OFFICE
CERTIFICATE OF CORRECTION

| | |
|---|---|
| PATENT NO. | : 7,422,737 B1 |
| APPLICATION NO. | : 10/657673 |
| DATED | : September 9, 2008 |
| INVENTOR(S) | : Nussinovitch et al. |

It is certified that error appears in the above-identified patent and that said Letters Patent is hereby corrected as shown below:

<u>Title Page</u>:
Item (73) Assignee, change "Yissam" to -- Yissum --. The name of the assignee will then correctly appear as -- Yissum Research Development Company of the Hebrew University of Jerusalem --.

Signed and Sealed this

Twenty-first Day of October, 2008

JON W. DUDAS
*Director of the United States Patent and Trademark Office*